UD012017973B2

United States Patent
Kilma et al.

(10) Patent No.: US 12,017,973 B2
(45) Date of Patent: Jun. 25, 2024

(54) AMINO ACID BASED SURFACTANTS AS FORMULANTS FOR BIOCIDES

(71) Applicant: BASF SE, Ludwigshafen am Rhein (DE)

(72) Inventors: Rodney F. Kilma, Cincinnati, OH (US); Dean A. Oester, Cincinnati, OH (US); Timothy H. Anderson, Cincinnati, OH (US); Mahmud Mustaqim Hussain, Wyandotte, MI (US)

(73) Assignee: BASF SE, Ludwigshafen am Rhein (DE)

( * ) Notice: Subject to any disclaimer, the term of this patent is extended or adjusted under 35 U.S.C. 154(b) by 478 days.

(21) Appl. No.: 17/253,773

(22) PCT Filed: Jun. 11, 2019

(86) PCT No.: PCT/EP2019/065186
§ 371 (c)(1),
(2) Date: Dec. 18, 2020

(87) PCT Pub. No.: WO2019/243112
PCT Pub. Date: Dec. 26, 2019

(65) Prior Publication Data
US 2021/0261494 A1    Aug. 26, 2021

Related U.S. Application Data

(60) Provisional application No. 62/688,652, filed on Jun. 22, 2018.

(30) Foreign Application Priority Data

Jul. 18, 2018   (EP) .................................... 18184077

(51) Int. Cl.
| C07C 229/36 | (2006.01) |
| A01N 25/30 | (2006.01) |
| A01N 37/46 | (2006.01) |
| A01N 41/06 | (2006.01) |

(52) U.S. Cl.
CPC ............ *C07C 229/36* (2013.01); *A01N 25/30* (2013.01); *A01N 37/46* (2013.01)

(58) Field of Classification Search
CPC ...... C07C 229/36; A01N 25/30; A01N 37/46; A01N 41/06
See application file for complete search history.

(56) References Cited

U.S. PATENT DOCUMENTS

| 5,084,087 A | 1/1992 | Hazen et al. |
| 5,260,260 A | 11/1993 | Gednalske et al. |
| 5,521,144 A | 5/1996 | Farr et al. |
| 5,554,644 A | 9/1996 | Horwell et al. |
| 2005/0106644 A1 | 5/2005 | Cairns et al. |

FOREIGN PATENT DOCUMENTS

| CN | 102907422 A | 2/2013 |
| EP | 0278787 A1 | 8/1988 |
| EP | 1023835 A1 | 8/2000 |
| JP | S5824547 A | 2/1983 |
| WO | 2004031129 A2 | 4/2004 |

OTHER PUBLICATIONS

International Search Report and Written Opinion for Corresponding PCT/EP2019/065186 dated Jul. 25, 2019, 13 pages.
Al-Sabagh, et al., "Synthesis of Some Novel Nonionic Ethoxylated Surfactants Based on a-Amino Acids and Investigation of Their Surface Active Properties", Journal of Dispersion Science and Technology, vol. 30, Issue 3, Feb. 23, 2009, pp. 427-438.
Chen, et al., "Features of Thiolated Ligands Promoting Resistance to Ligand Exchange in Self-Assembled Monolayers on Gold Nanoparticles", Australian Journal of Chemistry, vol. 65, Issue 3, 2011, pp. 266-274.
Database WPI Week 201343, Thomson Scientific, retrieved from STN Database accession No. 2013-H19266, XP002786829, Feb. 6, 2013, 2 pages.
Ding, et al., "PEG prodrug of gambogic acid: Amino acid and dipeptide spacer effects", Polymer, vol. 53, Issue 8, Apr. 2012, pp. 1694-1702.
European Search Report for EP Patent Application No. 18184077.8, dated Dec. 7, 2018, 8 pages.
Giraud-Clenet, et al., "Preparation, par hydroxyethylation selective, des acides alpha-amines N-beta-hydroxyethyles", Comptes rendus hebdomadaires des séances de l'Académie des sciences. Série C: Sciences Chimiques, vol. 268, 1969, pp. 117-120.
Kuwamura, et al., "Surfactants with Amino Linkage between the Hydrophilic and Hydrophobic Groups. I. Synthesis of Various Types of Surfactants from N-Acyl-alpha-Amino Acids and Their Properties", Journal of Japan Oil Chemists Society, vol. 34, Issue 8, 1985, pp. 626-633.
Muneyuki, et al., "Peptide Synthesis Using Enzyme as Synthetic Catalyst-Synthesis of New Water-Soluble Ester Substrates and Enzyme Immobilization", Nippo Kagaku Kaishi: Journal of the Chemical Society of Japan, Issue 9, 1983, pp. 1336-1344.
Peet, et al., "Hydroxyoxazolidines as α-aminoacetaldehyde equivalents: Novel inhibitors of calpain", Bioorganic & Medicinal Chemistry Letters, vol. 9, Issue 16, Aug. 16, 1999, pp. 2365-2370.
Prabhudesai, et al., "Synthesis of mixed diesters of ethanediol with N-acyl amino acids and fatty acids", Chemistry and Physics of Lipids, vol. 22, Issue 1, Aug. 1978, pp. 71-77.

*Primary Examiner* — Trevor Love
(74) *Attorney, Agent, or Firm* — Armstrong Teasdale LLP

(57) ABSTRACT

Described herein are alkoxylated compounds of general formula (I) and their use as adjuvant in the treatment of soil and plants. Also described are a composition including at least one biocide and at least one compound of general formula (I), as well as a method for improving the growth and health of plants by treating the crops with the composition including the compounds of general formula (I).

18 Claims, No Drawings

AMINO ACID BASED SURFACTANTS AS FORMULANTS FOR BIOCIDES

CROSS-REFERENCE TO RELATED APPLICATIONS

This application is a U.S. National Phase Application of International Patent Application No. PCT/EP2019/065186, filed Jun. 11, 2019, which claims the benefit of priority to U.S. Provisional Patent Application No. 62/688,652, filed Jun. 22, 2018, and to European Patent Application No. 18184077.8, filed Jul. 18, 2018, the entire contents of each of which are hereby incorporated by reference herein.

FIELD OF THE INVENTION

The presently claimed invention relates to alkoxylated compounds of general formula (I) and to their use as adjuvant in the treatment of soil and plants. The presently claimed invention further relates to a composition comprising at least one biocide and at least one compound of general formula (I). The presently claimed invention also relates to a method for improving the growth and health of plants by treating the crops with the composition comprising the compounds of general formula (I).

BACKGROUND OF THE INVENTION

Biocides such as fungicides, insecticides and herbicides, are important auxiliary agents for agriculture in order to protect crops and to increase their quality and harvest yield. An efficient uptake of the active ingredient by the plant is of particular importance for the activity of an agrochemical composition. If this uptake is via the leaf, it constitutes a complex translocation process, where the active substance, for example, a herbicide, must first penetrate the waxy cuticular of the leaf and subsequently diffuse, via the cuticular, into the tissue underneath, to the actual site of action. It is generally known and agricultural practice to add certain adjuvants to formulations in order to improve the activity of the latter. Advantageously, this allows the amounts of active ingredient in the formulation to be reduced while maintaining the same activity, thereby being able to minimize costs and, optionally, operating within existing legislation. In individual cases, this also allows the spectrum of the active ingredient to be widened, since plants whose treatment with a specific active ingredient without addition was only possible to an unsatisfactory extent, are now capable of being subjected to such a treatment as the result of the addition of certain auxiliaries.

In agriculture, alkyl phenol ethoxylates (APE) are used as adjuvants and co-formulated with biocides. They are used in the formulation of biocides for agricultural pest control concentrates or are a component of tank mix adjuvants for inclusion in the spray tank when agricultural pest control concentrates are diluted to assist in the activity of the biocide upon application to the target pest. Alkyl phenol ethoxylates (APE) are non-ionic surfactants containing alkyl chain bound to phenyl ring and a chain of repeating ethoxylate units, ranging from 1 to 100. The most commonly used APE is nonyl phenyl ethoxylate (NPE). NPEs influence the wetting, adhesion and spreading of biocide. They also break the waxy plant cuticular and improve the penetration of the biocide into the cuticular.

U.S. Pat. No. 5,084,087 A describes crop oil concentrates comprising (a) one or more herbicides; (b) an emulsifier component which is a combination of (i) a polyoxyalkylene nonionic surfactant which can be a polyoxyethylene ether of alkylphenol; and (ii) an anionic surfactant; (c) an optional second nonionic surfactant, and (d) a lower alkanol ester of a long chain fatty acid.

U.S. Pat. No. 5,521,144 A provides an adjuvant composition for use with pesticides comprising acidulated soap stock, (which is a by-product of alkali refining of crude vegetable or animal to remove the free fatty acid from the triglyceride) and surfactants. Preferred surfactants include nonionic surfactants such as alkylphenol ethoxylates (APEs) or blends of alcohol ethoxylates and glycol ethers.

U.S. Pat. No. 5,260,260 A discloses an improved herbicidal mixture comprising (a) a compatible herbicide; (b) acidulated soybean soapstock; and (c) a nonionic surfactant blend comprising nonoxynol which is an alpha-(nonylphenol) ethoxylate (APE).

A. M. Al-Sabagh et al. discloses the synthesis of novel nonionic ethoxylated surfactants based on amino acids (Journal of Dispersion Science and Technology, 30: 427-438, 2009).

Though APEs have been used in agricultural formulation for a long time, they are subject to increasing environmental regulation aimed at reducing their consumption. NPEs do not exhibit the high levels of toxicity, estrogenic activity or environmental persistence associated with nonyl phenol (NP). However, in the environment NPEs degrade to nonyl phenol (NP) and, thus, the release of NPEs to the environment from agricultural products ultimately leads to the introduction of more highly toxic and persistent NP residues. NPs are known to bioaccumulate and express estrogenic properties. The Environmental Protection Agency (EPA) has proposed to add a nonylphenol ethoxylates (NPEs) category to the list of toxic chemicals.

Therefore, it is an object of the presently claimed invention to provide an adjuvant compound which is environment friendly and which has all the attributes of an adjuvant, namely capable of increasing the effective contact area of biocides on the leaves by reducing the surface tension, effective wetting property to aid the adhesion and spreading of a formulation, ability to break the waxy plant cuticular and improve the penetration of the biocide into the cuticular.

SUMMARY OF THE INVENTION

Surprisingly, it was found that certain non-ionic surfactants based on naturally occurring α-amino acids are efficient wetting and emulsifying agents and act as an adjuvant in the treatment of plants.

Thus, in an aspect the presently claimed invention relates to a compound of general formula (I)

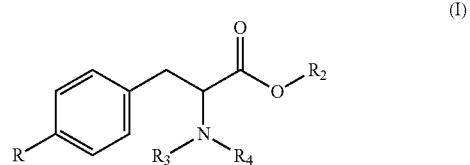

(I)

wherein,

R denotes H, OH or $OR_5$, wherein $R_5$ is $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

and

R$_2$ denotes linear or branched, substituted or unsubstituted C$_1$-C$_{16}$ alkyl or linear or branched, substituted or unsubstituted C$_2$-C$_{16}$ alkenyl;

R$_3$ denotes H or (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

R$_4$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

or

R$_2$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

R$_3$ denotes H;

R$_4$ denotes —C(=O)R$_1$ wherein R$_1$ is linear or branched, unsubstituted C$_2$-C$_{16}$ alkyl.

In another aspect, the presently claimed invention relates to the use of the at least one compound of general formula (I), as described herein above, as adjuvant in the treatment of soil and plants.

In another aspect, the presently claimed invention relates to a method for improving the growth and health of plants characterized in that the crops are treated with the at least one compound of general formula (I), as described herein above.

In still another aspect, the presently claimed invention relates to a composition comprising
(i) at least one biocide and
(ii) at least one compound of general formula (I), as described herein above.

In another aspect, the presently claimed invention relates to a method of forming a stable composition comprising the step of mixing the at least one compound of general formula (I) with the at least one biocide.

In another aspect, the presently claimed invention relates to a method of forming a stable composition comprising adding the at least one compound of general formula (I) to a tank as a tank mix additive, the tank comprising the biocide.

In another aspect, the presently claimed invention relates to the use of the composition comprising the at least one biocide and the at least one compound of general formula (I) as adjuvant in the treatment of soil and plants.

In yet another aspect, the presently claimed invention relates to a method for improving the growth and health of plants characterized in that the crops are treated with the composition comprising the at least one biocide and the at least one compound of general formula (I).

DETAILED DESCRIPTION OF THE INVENTION

Before the present compositions and formulations of the invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(A)", "(B)" and "(C)" or "(a)", "(b)", "(c)", "(d)", "i", "ii" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the presently claimed invention. Thus, appearances of the phrases "in one embodiment" or "in an embodiment" in various places throughout this specification are not necessarily all referring to the same embodiment, but may do so. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In one aspect, the presently claimed invention relates to a compound of general formula (I)

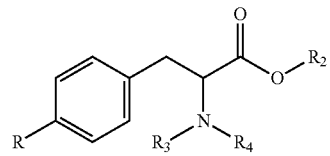

(I)

wherein

R denotes H, OH or OR$_5$, wherein R$_5$ is (AO)$_n$—H wherein (AO) is independently CH$_2$—CH$_2$—O, CH(CH$_3$)—CH$_2$—O, CH$_2$—CH(CH$_3$)—O, CH($C_2H_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;
and R$_2$ denotes linear or branched, substituted or unsubstituted C$_1$-C$_{16}$ alkyl or linear or branched, substituted or unsubstituted C$_2$-C$_{16}$ alkenyl;

R$_3$ denotes H or (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

R$_4$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

or

R$_2$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

R$_3$ denotes H;

R$_4$ denotes —C(=O)R$_1$ wherein R$_1$ is linear or branched, unsubstituted C$_2$-C$_{16}$ alkyl.

For the purposes of the presently claimed invention, the term "C$_1$-C$_{16}$-alkyl" covers acyclic saturated hydrocarbon residues, which may be linear or branched and unsubstituted or at least mono-substituted with, as in the case of C$_1$-C$_{16}$-alkyl, 1 to 16 (i.e. 1, 2, 3, 4, 5, 6, 7, 8, 9, 10, 11, 12, 13, 14, 15 or 16) carbon atoms. If one or more of the substituents denote an alkyl residue which is mono- or polysubstituted, this may preferably be substituted with optionally 1, 2, 3, 4 or 5, particularly preferably with 1, 2 or 3, substituents mutually independently selected from the group of F, Cl, Br, I, —NO$_2$, —CN, —OH, —SH, —NH$_2$, —N(C$_{1-5}$-alkyl)$_2$, —N(C$_{1-5}$-alkyl-OH)$_2$, —N(C$_{1-5}$-alkyl)(phenyl), —N(C$_{1-5}$-alkyl)(CH$_2$-phenyl), —N(C$_{1-5}$alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated-C-s alkyl residues may in each case be linear or branched and the above-stated phenyl residues may preferably be substituted with 1, 2, 3, 4 or 5 substituents mutually independently selected from the group of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl. Particularly preferred substituents may be selected mutually independently from the group of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$). As used herein, "branched" denotes a chain of atoms with one or more side chains attached to it. Branching occurs by the replacement of a substituent, e.g., a hydrogen atom, with a covalently bonded alkyl radical.

For the purpose of the presently claimed invention, the term "alkenyl" covers acyclic unsaturated hydrocarbon residues, which may be linear or branched and unsubstituted or at least mono-substituted and comprise at least one double band, preferably 1, 2 or 3 double bonds, with, as in the case of C$_2$-C$_{16}$ alkenyl, 2 to 16 (i.e. 2, 3, 4, 5, 6, 7, 8, 9, 10, 11, 12, 13, 14, 15 or 16) carbon atoms or with, as in the case of C$_2$-C$_6$ alkenyl, 2 to 6 (i.e. 2, 3, 4, 5 or 6) C atoms. If one or more of the substituents denote an alkenyl residue which is mono- or polysubstituted, this may preferably be substituted with optionally 1, 2, 3, 4 or 5, particularly preferably with 1, 2 or 3, substituents mutually independently selected from the group of F, Cl, Br, I, —NO$_2$, —CN, —OH, —SH, —NH$_2$, —N(C$_{1-5}$-alkyl)$_2$, —N(C$_1$-s-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated-C$_{1-5}$ alkyl residues may in each case be linear or branched and the above-stated phenyl residues may preferably be substituted with 1, 2, 3, 4 or 5 substituents mutually independently selected from the group of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl. Particularly preferred substituents may be selected mutually independently from the group of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Compound of General Formula (I)

The compound of general formula (I) has the following structure

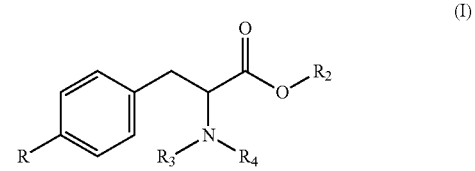

(I)

wherein

R denotes H, OH or OR$_5$, wherein R$_5$ is (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

and

R$_2$ denotes linear or branched, substituted or unsubstituted C$_1$-C$_{16}$ alkyl or linear or branched, substituted or unsubstituted C$_2$-C$_{16}$ alkenyl;

R$_3$ denotes H or (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

R$_4$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 1 to 39;

or

R$_2$ denotes (AO)$_n$—H wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—

O, $CH_2C(CH_3)_2$—O or $CH_2$—$CH(C_2H_5)$—O, and n is an integer in the range from 1 to 39;

$R_3$ denotes H;

$R_4$ denotes —C(=O)$R_1$ wherein $R_1$ is linear or branched, unsubstituted $C_2$-$C_{16}$ alkyl.

Preferably, R is selected from H, OH or $OR_5$.

Particularly preferably, R is selected from H or OH.

In an embodiment, the compound of general formula (I) is

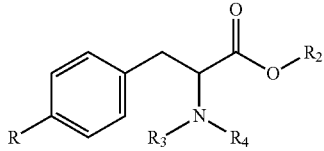

(I)

wherein

R denotes H, OH or $OR_5$, wherein $R_5$ is $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

and $R_2$ denotes linear or branched, substituted or unsubstituted $C_1$-$C_{16}$ alkyl or linear or branched, substituted or unsubstituted $C_2$-$C_{16}$ alkenyl;

$R_3$ denotes H or $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

$R_4$ denotes $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

Preferably $R_2$ is selected from the group of methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, isotetradecyl, isopentadecyl and isohexadecyl.

More preferably, $R_2$ is selected from the group of methyl, ethyl, n-propyl, n-butyl, n-hexyl, n-dodecyl, n-tetradecyl, isopropyl, isobutyl, isohexyl, isododecyl and iso-tetradecyl.

Preferably $R_3$ is $(AO)_n$—H, wherein (AO) is selected from the group of $CH_2$—$CH_2$—O, $CH(CH_3)CH_2$—O and $CH_2$—$CH(CH_3)$—O, and more preferably (AO) is $CH_2$—$CH_2$—O.

Preferably, $R_4$ is $(AO)_n$—H, wherein (AO) is selected from the group of $CH_2$—$CH_2$—O, $CH(CH_3)CH_2$—O and $CH_2$—$CH(CH_3)$—O, and more preferably (AO) is $CH_2$—$CH_2$—O.

In a preferred embodiment, n is an integer in the range of 1 to 38 or 1 to 37 or 1 to 36 or 1 to 35 or 1 to 34 or 1 to 35 or 1 to 34 or 1 to 33 or 1 to 32 or 1 to 31 or 1 to 30 or 2 to 38 or 2 to 37 or 2 to 36 or 2 to 35 or 2 to 34 or 2 to 35 or 2 to 34 or 2 to 33 or 2 to 32 or 2 to 31 or 2 to 30 or 3 to 38 more preferably in the range of 4 to 37 or 5 to 37 or even more preferably in the range of 5 to 36 or 5 to 35 or 5 to 34 or 6 to 36 or 6 to 35 or 6 to 34 or 7 to 36 or 7 to 35 or 7 to 34 still more preferably in the range of 8 to 33 or 8 to 32 or 8 to 31 or 8 to 30 or 9 to 33 or 9 to 32 or 9 to 31 or 9 to 30 and most preferably in the range of 9 to 28 or 9 to 26 or 9 to 24 or 9 to 22 or 9 to 20 or 9 to 18 or 9 to 16 or 9 to 14 or 9 to 12 or 10 to 30 or 10 to 28 or 10 to 26 or 10 to 24 or 10 to 22 or 10 to 20 or 10 to 18 or 10 to 16.

Preferably, the at least one compound of general formula (I) is a compound of general formula (Ia)

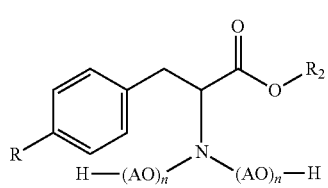

(Ia)

wherein

R denotes H or OH;

$R_2$ denotes linear or branched, unsubstituted $C_1$-$C_{16}$ alkyl;

(AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

Particularly preferably, compounds of general formula (Ia) are compounds as defined in Table 1 to Table 39.

Table-1

Compound of general formula (Ia) wherein n=1 and combination of variables $R_2$, AO and R correspond to each row of Table A Table-2

Compound of general formula (Ia) wherein n=2 and combination of variables $R_2$, AO and R correspond to each row of Table A Table-3

Compound of general formula (Ia) wherein n=3 and combination of variables $R_2$, AO and R correspond to each row of Table A Table-4

Compound of general formula (Ia) wherein n=4 and combination of variables $R_2$, AO and R correspond to each row of Table A Table-5

Compound of general formula (Ia) wherein n=5 and combination of variables $R_2$, AO and R correspond to each row of Table A Table-6

Compound of general formula (Ia) wherein n=6 and combination of variables $R_2$, AO and R correspond to each row of Table A Table-7

Compound of general formula (Ia) wherein n=7 and combination of variables $R_2$, AO and R correspond to each row of Table A Table-8

Compound of general formula (Ia) wherein n=8 and combination of variables $R_2$, AO and R correspond to each row of Table A Table-9

Compound of general formula (Ia) wherein n=9 and combination of variables $R_2$, AO and R correspond to each row of Table A Table-10
Compound of general formula (Ia) wherein n=10 and combination of variables $R_2$, AO and R correspond to each row of Table A Table-11
Compound of general formula (Ia) wherein n=11 and combination of variables $R_2$, AO and R correspond to each row of Table A Table-12
Compound of general formula (Ia) wherein n=12 and combination of variables $R_2$, AO and R correspond to each row of Table A Table-13
Compound of general formula (Ia) wherein n=13 and combination of variables $R_2$, AO and R correspond to each row of Table A Table-14
Compound of general formula (Ia) wherein n=14 and combination of variables $R_2$, AO and R correspond to each row of Table A Table-15
Compound of general formula (Ia) wherein n=15 and combination of variables $R_2$, AO and R correspond to each row of Table A Table-16
Compound of general formula (Ia) wherein n=16 and combination of variables $R_2$, AO and R correspond to each row of Table A Table-17
Compound of general formula (Ia) wherein n=17 and combination of variables $R_2$, AO and R correspond to each row of Table A Table-18
Compound of general formula (Ia) wherein n=18 and combination of variables $R_2$, AO and R correspond to each row of Table A Table-19
Compound of general formula (Ia) wherein n=19 and combination of variables $R_2$, AO and R correspond to each row of Table A Table-20
Compound of general formula (Ia) wherein n=20 and combination of variables $R_2$, AO and R correspond to each row of Table A Table-21
Compound of general formula (Ia) wherein n=21 and combination of variables $R_2$, AO and R correspond to each row of Table A Table-22
Compound of general formula (Ia) wherein n=22 and combination of variables $R_2$, AO and R correspond to each row of Table A Table-23
Compound of general formula (Ia) wherein n=23 and combination of variables $R_2$, AO and R correspond to each row of Table A Table-24
Compound of general formula (Ia) wherein n=24 and combination of variables $R_2$, AO and R correspond to each row of Table A Table-25
Compound of general formula (Ia) wherein n=25 and combination of variables $R_2$, AO and R correspond to each row of Table A Table-26
Compound of general formula (Ia) wherein n=26 and combination of variables $R_2$, AO and R correspond to each row of Table A Table-27
Compound of general formula (Ia) wherein n=27 and combination of variables $R_2$, AO and R correspond to each row of Table A Table-28
Compound of general formula (Ia) wherein n=28 and combination of variables $R_2$, AO and R correspond to each row of Table A Table-29
Compound of general formula (Ia) wherein n=29 and combination of variables $R_2$, AO and R correspond to each row of Table A Table-30
Compound of general formula (Ia) wherein n=30 and combination of variables $R_2$, AO and R correspond to each row of Table A Table-31
Compound of general formula (Ia) wherein n=31 and combination of variables $R_2$, AO and R correspond to each row of Table A Table-32
Compound of general formula (Ia) wherein n=32 and combination of variables $R_2$, AO and R correspond to each row of Table A Table-33
Compound of general formula (Ia) wherein n=33 and combination of variables $R_2$, AO and R correspond to each row of Table A Table-34
Compound of general formula (Ia) wherein n=34 and combination of variables $R_2$, AO and R correspond to each row of Table A Table-35
Compound of general formula (Ia) wherein n=35 and combination of variables $R_2$, AO and R correspond to each row of Table A Table-36
Compound of general formula (Ia) wherein n=36 and combination of variables $R_2$, AO and R correspond to each row of Table A Table-37
Compound of general formula (Ia) wherein n=37 and combination of variables $R_2$, AO and R correspond to each row of Table A Table-38
Compound of general formula (Ia) wherein n=38 and combination of variables $R_2$, AO and R correspond to each row of Table A Table-39
Compound of general formula (Ia) wherein n=39 and combination of variables $R_2$, AO and R correspond to each row of Table A

TABLE-A

| row | $R_2$ | AO | R |
|---|---|---|---|
| 1. | $CH_3$ | $CH_2-CH_2-O$ | H |
| 2. | $CH_3$ | $CH_2-CH_2-O$ | OH |
| 3. | $CH_3$ | $CH(CH_3)-CH_2-O$ | H |
| 4. | $CH_3$ | $CH(CH_3)-CH_2-O$ | OH |
| 5. | $CH_3$ | $CH_2-CH(CH_3)-O$ | H |
| 6. | $CH_3$ | $CH_2-CH(CH_3)-O$ | OH |
| 7. | $CH_3$ | $CH(C_2H_5)-CH_2-O$ | H |

TABLE-A-continued

| row | R₂ | AO | R |
|---|---|---|---|
| 8. | $CH_3$ | $CH(C_2H_5)-CH_2-O$ | OH |
| 9. | $CH_3$ | $C(CH_3)_2-CH_2-O$ | H |
| 10. | $CH_3$ | $C(CH_3)_2-CH_2-O$ | OH |
| 11. | $CH_3$ | $CH_2C(CH_3)_2-O$ | H |
| 12. | $CH_3$ | $CH_2C(CH_3)_2-O$ | OH |
| 13. | $CH_3$ | $CH_2-CH(C_2H_5)-O$ | H |
| 14. | $CH_3$ | $CH_2-CH(C_2H_5)-O$ | OH |
| 15. | $C_2H_5$ | $CH_2-CH_2-O$ | H |
| 16. | $C_2H_5$ | $CH_2-CH_2-O$ | OH |
| 17. | $C_2H_5$ | $CH(CH_3)-CH_2-O$ | H |
| 18. | $C_2H_5$ | $CH(CH_3)-CH_2-O$ | OH |
| 19. | $C_2H_5$ | $CH_2-CH(CH_3)-O$ | H |
| 20. | $C_2H_5$ | $CH_2-CH(CH_3)-O$ | OH |
| 21. | $C_2H_5$ | $CH(C_2H_5)-CH_2-O$ | H |
| 22. | $C_2H_5$ | $CH(C_2H_5)-CH_2-O$ | OH |
| 23. | $C_2H_5$ | $C(CH_3)_2-CH_2-O$ | H |
| 24. | $C_2H_5$ | $C(CH_3)_2-CH_2-O$ | OH |
| 25. | $C_2H_5$ | $CH_2C(CH_3)_2-O$ | H |
| 26. | $C_2H_5$ | $CH_2C(CH_3)_2-O$ | OH |
| 27. | $C_2H_5$ | $CH_2-CH(C_2H_5)-O$ | H |
| 28. | $C_2H_5$ | $CH_2-CH(C_2H_5)-O$ | OH |
| 29. | $n-C_3H_7$ | $CH_2-CH_2-O$ | H |
| 30. | $n-C_3H_7$ | $CH_2-CH_2-O$ | OH |
| 31. | $n-C_3H_7$ | $CH(CH_3)-CH_2-O$ | H |
| 32. | $n-C_3H_7$ | $CH(CH_3)-CH_2-O$ | OH |
| 33. | $n-C_3H_7$ | $CH_2-CH(CH_3)-O$ | H |
| 34. | $n-C_3H_7$ | $CH_2-CH(CH_3)-O$ | OH |
| 35. | $n-C_3H_7$ | $CH(C_2H_5)-CH_2-O$ | H |
| 36. | $n-C_3H_7$ | $CH(C_2H_5)-CH_2-O$ | OH |
| 37. | $n-C_3H_7$ | $C(CH_3)_2-CH_2-O$ | H |
| 38. | $n-C_3H_7$ | $C(CH_3)_2-CH_2-O$ | OH |
| 39. | $n-C_3H_7$ | $CH_2C(CH_3)_2-O$ | H |
| 40. | $n-C_3H_7$ | $CH_2C(CH_3)_2-O$ | OH |
| 41. | $n-C_3H_7$ | $CH_2-CH(C_2H_5)-O$ | H |
| 42. | $n-C_3H_7$ | $CH_2-CH(C_2H_5)-O$ | OH |
| 43. | $n-C_4H_9$ | $CH_2-CH_2-O$ | H |
| 44. | $n-C_4H_9$ | $CH_2-CH_2-O$ | OH |
| 45. | $n-C_4H_9$ | $CH(CH_3)-CH_2-O$ | H |
| 46. | $n-C_4H_9$ | $CH(CH_3)-CH_2-O$ | OH |
| 47. | $n-C_4H_9$ | $CH_2-CH(CH_3)-O$ | H |
| 48. | $n-C_4H_9$ | $CH_2-CH(CH_3)-O$ | OH |
| 49. | $n-C_4H_9$ | $CH(C_2H_5)-CH_2-O$ | H |
| 50. | $n-C_4H_9$ | $CH(C_2H_5)-CH_2-O$ | OH |
| 51. | $n-C_4H_9$ | $C(CH_3)_2-CH_2-O$ | H |
| 52. | $n-C_4H_9$ | $C(CH_3)_2-CH_2-O$ | OH |
| 53. | $n-C_4H_9$ | $CH_2C(CH_3)_2-O$ | H |
| 54. | $n-C_4H_9$ | $CH_2C(CH_3)_2-O$ | OH |
| 55. | $n-C_4H_9$ | $CH_2-CH(C_2H_5)-O$ | H |
| 56. | $n-C_4H_9$ | $CH_2-CH(C_2H_5)-O$ | OH |
| 57. | $n-C_5H_{11}$ | $CH_2-CH_2-O$ | H |
| 58. | $n-C_5H_{11}$ | $CH_2-CH_2-O$ | OH |
| 59. | $n-C_5H_{11}$ | $CH(CH_3)-CH_2-O$ | H |
| 60. | $n-C_5H_{11}$ | $CH(CH_3)-CH_2-O$ | OH |
| 61. | $n-C_5H_{11}$ | $CH_2-CH(CH_3)-O$ | H |
| 62. | $n-C_5H_{11}$ | $CH_2-CH(CH_3)-O$ | OH |
| 63. | $n-C_5H_{11}$ | $CH(C_2H_5)-CH_2-O$ | H |
| 64. | $n-C_5H_{11}$ | $CH(C_2H_5)-CH_2-O$ | OH |
| 65. | $n-C_5H_{11}$ | $C(CH_3)_2-CH_2-O$ | H |
| 66. | $n-C_5H_{11}$ | $C(CH_3)_2-CH_2-O$ | OH |
| 67. | $n-C_5H_{11}$ | $CH_2C(CH_3)_2-O$ | H |
| 68. | $n-C_5H_{11}$ | $CH_2C(CH_3)_2-O$ | OH |
| 69. | $n-C_5H_{11}$ | $CH_2-CH(C_2H_5)-O$ | H |
| 70. | $n-C_5H_{11}$ | $CH_2-CH(C_2H_5)-O$ | OH |
| 71. | $n-C_6H_{13}$ | $CH_2-CH_2-O$ | H |
| 72. | $n-C_6H_{13}$ | $CH_2-CH_2-O$ | OH |
| 73. | $n-C_6H_{13}$ | $CH(CH_3)-CH_2-O$ | H |
| 74. | $n-C_6H_{13}$ | $CH(CH_3)-CH_2-O$ | OH |
| 75. | $n-C_6H_{13}$ | $CH_2-CH(CH_3)-O$ | H |
| 76. | $n-C_6H_{13}$ | $CH_2-CH(CH_3)-O$ | OH |
| 77. | $n-C_6H_{13}$ | $CH(C_2H_5)-CH_2-O$ | H |
| 78. | $n-C_6H_{13}$ | $CH(C_2H_5)-CH_2-O$ | OH |
| 79. | $n-C_6H_{13}$ | $C(CH_3)_2-CH_2-O$ | H |
| 80. | $n-C_6H_{13}$ | $C(CH_3)_2-CH_2-O$ | OH |
| 81. | $n-C_6H_{13}$ | $CH_2C(CH_3)_2-O$ | H |
| 82. | $n-C_6H_{13}$ | $CH_2C(CH_3)_2-O$ | OH |
| 83. | $n-C_6H_{13}$ | $CH_2-CH(C_2H_5)-O$ | H |
| 84. | $n-C_6H_{13}$ | $CH_2-CH(C_2H_5)-O$ | OH |
| 85. | $n-C_7H_{15}$ | $CH_2-CH_2-O$ | H |
| 86. | $n-C_7H_{15}$ | $CH_2-CH_2-O$ | OH |
| 87. | $n-C_7H_{15}$ | $CH(CH_3)-CH_2-O$ | H |
| 88. | $n-C_7H_{15}$ | $CH(CH_3)-CH_2-O$ | OH |
| 89. | $n-C_7H_{15}$ | $CH_2-CH(CH_3)-O$ | H |
| 90. | $n-C_7H_{15}$ | $CH_2-CH(CH_3)-O$ | OH |
| 91. | $n-C_7H_{15}$ | $CH(C_2H_5)-CH_2-O$ | H |
| 92. | $n-C_7H_{15}$ | $CH(C_2H_5)-CH_2-O$ | OH |
| 93. | $n-C_7H_{15}$ | $C(CH_3)_2-CH_2-O$ | H |
| 94. | $n-C_7H_{15}$ | $C(CH_3)_2-CH_2-O$ | OH |
| 95. | $n-C_7H_{15}$ | $CH_2C(CH_3)_2-O$ | H |
| 96. | $n-C_7H_{15}$ | $CH_2C(CH_3)_2-O$ | OH |
| 97. | $n-C_7H_{15}$ | $CH_2-CH(C_2H_5)-O$ | H |
| 98. | $n-C_7H_{15}$ | $CH_2-CH(C_2H_5)-O$ | OH |
| 99. | $n-C_8H_{17}$ | $CH_2-CH_2-O$ | H |
| 100. | $n-C_8H_{17}$ | $CH_2-CH_2-O$ | OH |
| 101. | $n-C_8H_{17}$ | $CH(CH_3)-CH_2-O$ | H |
| 102. | $n-C_8H_{17}$ | $CH(CH_3)-CH_2-O$ | OH |
| 103. | $n-C_8H_{17}$ | $CH_2-CH(CH_3)-O$ | H |
| 104. | $n-C_8H_{17}$ | $CH_2-CH(CH_3)-O$ | OH |
| 105. | $n-C_8H_{17}$ | $CH(C_2H_5)-CH_2-O$ | H |
| 106. | $n-C_8H_{17}$ | $CH(C_2H_5)-CH_2-O$ | OH |
| 107. | $n-C_8H_{17}$ | $C(CH_3)_2-CH_2-O$ | H |
| 108. | $n-C_8H_{17}$ | $C(CH_3)_2-CH_2-O$ | OH |
| 109. | $n-C_8H_{17}$ | $CH_2C(CH_3)_2-O$ | H |
| 110. | $n-C_8H_{17}$ | $CH_2C(CH_3)_2-O$ | OH |
| 111. | $n-C_8H_{17}$ | $CH_2-CH(C_2H_5)-O$ | H |
| 112. | $n-C_8H_{17}$ | $CH_2-CH(C_2H_5)-O$ | OH |
| 113. | $n-C_9H_{19}$ | $CH_2-CH_2-O$ | H |
| 114. | $n-C_9H_{19}$ | $CH_2-CH_2-O$ | OH |
| 115. | $n-C_9H_{19}$ | $CH(CH_3)-CH_2-O$ | H |
| 116. | $n-C_9H_{19}$ | $CH(CH_3)-CH_2-O$ | OH |
| 117. | $n-C_9H_{19}$ | $CH_2-CH(CH_3)-O$ | H |
| 118. | $n-C_9H_{19}$ | $CH_2-CH(CH_3)-O$ | OH |
| 119. | $n-C_9H_{19}$ | $CH(C_2H_5)-CH_2-O$ | H |
| 120. | $n-C_9H_{19}$ | $CH(C_2H_5)-CH_2-O$ | OH |
| 121. | $n-C_9H_{19}$ | $C(CH_3)_2-CH_2-O$ | H |
| 122. | $n-C_9H_{19}$ | $C(CH_3)_2-CH_2-O$ | OH |
| 123. | $n-C_9H_{19}$ | $CH_2C(CH_3)_2-O$ | H |
| 124. | $n-C_9H_{19}$ | $CH_2C(CH_3)_2-O$ | OH |
| 125. | $n-C_9H_{19}$ | $CH_2-CH(C_2H_5)-O$ | H |
| 126. | $n-C_9H_{19}$ | $CH_2-CH(C_2H_5)-O$ | OH |
| 127. | $n-C_{10}H_{21}$ | $CH_2-CH_2-O$ | H |
| 128. | $n-C_{10}H_{21}$ | $CH_2-CH_2-O$ | OH |
| 129. | $n-C_{10}H_{21}$ | $CH(CH_3)-CH_2-O$ | H |
| 130. | $n-C_{10}H_{21}$ | $CH(CH_3)-CH_2-O$ | OH |
| 131. | $n-C_{10}H_{21}$ | $CH_2-CH(CH_3)-O$ | H |
| 132. | $n-C_{10}H_{21}$ | $CH_2-CH(CH_3)-O$ | OH |
| 133. | $n-C_{10}H_{21}$ | $CH(C_2H_5)-CH_2-O$ | H |
| 134. | $n-C_{10}H_{21}$ | $CH(C_2H_5)-CH_2-O$ | OH |
| 135. | $n-C_{10}H_{21}$ | $C(CH_3)_2-CH_2-O$ | H |
| 136. | $n-C_{10}H_{21}$ | $C(CH_3)_2-CH_2-O$ | OH |
| 137. | $n-C_{10}H_{21}$ | $CH_2C(CH_3)_2-O$ | H |
| 138. | $n-C_{10}H_{21}$ | $CH_2C(CH_3)_2-O$ | OH |
| 139. | $n-C_{10}H_{21}$ | $CH_2-CH(C_2H_5)-O$ | H |
| 140. | $n-C_{10}H_{21}$ | $CH_2-CH(C_2H_5)-O$ | OH |
| 141. | $n-C_{11}H_{23}$ | $CH_2-CH_2-O$ | H |
| 142. | $n-C_{11}H_{23}$ | $CH_2-CH_2-O$ | OH |
| 143. | $n-C_{11}H_{23}$ | $CH(CH_3)-CH_2-O$ | H |
| 144. | $n-C_{11}H_{23}$ | $CH(CH_3)-CH_2-O$ | OH |
| 145. | $n-C_{11}H_{23}$ | $CH_2-CH(CH_3)-O$ | H |
| 146. | $n-C_{11}H_{23}$ | $CH_2-CH(CH_3)-O$ | OH |
| 147. | $n-C_{11}H_{23}$ | $CH(C_2H_5)-CH_2-O$ | H |
| 148. | $n-C_{11}H_{23}$ | $CH(C_2H_5)-CH_2-O$ | OH |
| 149. | $n-C_{11}H_{23}$ | $C(CH_3)_2-CH_2-O$ | H |
| 150. | $n-C_{11}H_{23}$ | $C(CH_3)_2-CH_2-O$ | OH |
| 151. | $n-C_{11}H_{23}$ | $CH_2C(CH_3)_2-O$ | H |
| 152. | $n-C_{11}H_{23}$ | $CH_2C(CH_3)_2-O$ | OH |
| 153. | $n-C_{11}H_{23}$ | $CH_2-CH(C_2H_5)-O$ | H |
| 154. | $n-C_{11}H_{23}$ | $CH_2-CH(C_2H_5)-O$ | OH |
| 155. | $n-C_{12}H_{25}$ | $CH_2-CH_2-O$ | H |
| 156. | $n-C_{12}H_{25}$ | $CH_2-CH_2-O$ | OH |
| 157. | $n-C_{12}H_{25}$ | $CH(CH_3)-CH_2-O$ | H |
| 158. | $n-C_{12}H_{25}$ | $CH(CH_3)-CH_2-O$ | OH |
| 159. | $n-C_{12}H_{25}$ | $CH_2-CH(CH_3)-O$ | H |
| 160. | $n-C_{12}H_{25}$ | $CH_2-CH(CH_3)-O$ | OH |
| 161. | $n-C_{12}H_{25}$ | $CH(C_2H_5)-CH_2-O$ | H |
| 162. | $n-C_{12}H_{25}$ | $CH(C_2H_5)-CH_2-O$ | OH |
| 163. | $n-C_{12}H_{25}$ | $C(CH_3)_2-CH_2-O$ | H |

TABLE-A-continued

| row | R₂ | AO | R |
|---|---|---|---|
| 164. | n-C$_{12}$H$_{25}$ | C(CH$_3$)$_2$—CH$_2$—O | OH |
| 165. | n-C$_{12}$H$_{25}$ | CH$_2$C(CH$_3$)$_2$—O | H |
| 166. | n-C$_{12}$H$_{25}$ | CH$_2$C(CH$_3$)$_2$—O | OH |
| 167. | n-C$_{12}$H$_{25}$ | CH$_2$—CH(C$_2$H$_5$)—O | H |
| 168. | n-C$_{12}$H$_{25}$ | CH$_2$—CH(C$_2$H$_5$)—O | OH |
| 169. | n-C$_{13}$H$_{27}$ | CH$_2$—CH$_2$—O | H |
| 170. | n-C$_{13}$H$_{27}$ | CH$_2$—CH$_2$—O | OH |
| 171. | n-C$_{13}$H$_{27}$ | CH(CH$_3$)—CH$_2$—O | H |
| 172. | n-C$_{13}$H$_{27}$ | CH(CH$_3$)—CH$_2$—O | OH |
| 173. | n-C$_{13}$H$_{27}$ | CH$_2$—CH(CH$_3$)—O | H |
| 174. | n-C$_{13}$H$_{27}$ | CH$_2$—CH(CH$_3$)—O | OH |
| 175. | n-C$_{13}$H$_{27}$ | CH(C$_2$H$_5$)—CH$_2$—O | H |
| 176. | n-C$_{13}$H$_{27}$ | CH(C$_2$H$_5$)—CH$_2$—O | OH |
| 177. | n-C$_{13}$H$_{27}$ | C(CH$_3$)$_2$—CH$_2$—O | H |
| 178. | n-C$_{13}$H$_{27}$ | C(CH$_3$)$_2$—CH$_2$—O | OH |
| 179. | n-C$_{13}$H$_{27}$ | CH$_2$C(CH$_3$)$_2$—O | H |
| 180. | n-C$_{13}$H$_{27}$ | CH$_2$C(CH$_3$)$_2$—O | OH |
| 181. | n-C$_{13}$H$_{27}$ | CH$_2$—CH(C$_2$H$_5$)—O | H |
| 182. | n-C$_{13}$H$_{27}$ | CH$_2$—CH(C$_2$H$_5$)—O | OH |
| 183. | n-C$_{14}$H$_{29}$ | CH$_2$—CH$_2$—O | H |
| 184. | n-C$_{14}$H$_{29}$ | CH$_2$—CH$_2$—O | OH |
| 185. | n-C$_{14}$H$_{29}$ | CH(CH$_3$)—CH$_2$—O | H |
| 186. | n-C$_{14}$H$_{29}$ | CH(CH$_3$)—CH$_2$—O | OH |
| 187. | n-C$_{14}$H$_{29}$ | CH$_2$—CH(CH$_3$)—O | H |
| 188. | n-C$_{14}$H$_{29}$ | CH$_2$—CH(CH$_3$)—O | OH |
| 189. | n-C$_{14}$H$_{29}$ | CH(C$_2$H$_5$)—CH$_2$—O | H |
| 190. | n-C$_{14}$H$_{29}$ | CH(C$_2$H$_5$)—CH$_2$—O | OH |
| 191. | n-C$_{14}$H$_{29}$ | C(CH$_3$)$_2$—CH$_2$—O | H |
| 192. | n-C$_{14}$H$_{29}$ | C(CH$_3$)$_2$—CH$_2$—O | OH |
| 193. | n-C$_{14}$H$_{29}$ | CH$_2$C(CH$_3$)$_2$—O | H |
| 194. | n-C$_{14}$H$_{29}$ | CH$_2$C(CH$_3$)$_2$—O | OH |
| 195. | n-C$_{14}$H$_{29}$ | CH$_2$—CH(C$_2$H$_5$)—O | H |
| 196. | n-C$_{14}$H$_{29}$ | CH$_2$—CH(C$_2$H$_5$)—O | OH |
| 197. | n-C$_{15}$H$_{31}$ | CH$_2$—CH$_2$—O | H |
| 198. | n-C$_{15}$H$_{31}$ | CH$_2$—CH$_2$—O | OH |
| 199. | n-C$_{15}$H$_{31}$ | CH(CH$_3$)—CH$_2$—O | H |
| 200. | n-C$_{15}$H$_{31}$ | CH(CH$_3$)—CH$_2$—O | OH |
| 201. | n-C$_{15}$H$_{31}$ | CH$_2$—CH(CH$_3$)—O | H |
| 202. | n-C$_{15}$H$_{31}$ | CH$_2$—CH(CH$_3$)—O | OH |
| 203. | n-C$_{15}$H$_{31}$ | CH(C$_2$H$_5$)—CH$_2$—O | H |
| 204. | n-C$_{15}$H$_{31}$ | CH(C$_2$H$_5$)—CH$_2$—O | OH |
| 205. | n-C$_{15}$H$_{31}$ | C(CH$_3$)$_2$—CH$_2$—O | H |
| 206. | n-C$_{15}$H$_{31}$ | C(CH$_3$)$_2$—CH$_2$—O | OH |
| 207. | n-C$_{15}$H$_{31}$ | CH$_2$C(CH$_3$)$_2$—O | H |
| 208. | n-C$_{15}$H$_{31}$ | CH$_2$C(CH$_3$)$_2$—O | OH |
| 209. | n-C$_{15}$H$_{31}$ | CH$_2$—CH(C$_2$H$_5$)—O | H |
| 210. | n-C$_{15}$H$_{31}$ | CH$_2$—CH(C$_2$H$_5$)—O | OH |
| 211. | n-C$_{16}$H$_{33}$ | CH$_2$—CH$_2$—O | H |
| 212. | n-C$_{16}$H$_{33}$ | CH$_2$—CH$_2$—O | OH |
| 213. | n-C$_{16}$H$_{33}$ | CH(CH$_3$)—CH$_2$—O | H |
| 214. | n-C$_{16}$H$_{33}$ | CH(CH$_3$)—CH$_2$—O | OH |
| 215. | n-C$_{16}$H$_{33}$ | CH$_2$—CH(CH$_3$)—O | H |
| 216. | n-C$_{16}$H$_{33}$ | CH$_2$—CH(CH$_3$)—O | OH |
| 217. | n-C$_{16}$H$_{33}$ | CH(C$_2$H$_5$)—CH$_2$—O | H |
| 218. | n-C$_{16}$H$_{33}$ | CH(C$_2$H$_5$)—CH$_2$—O | OH |
| 219. | n-C$_{16}$H$_{33}$ | C(CH$_3$)$_2$—CH$_2$—O | H |
| 220. | n-C$_{16}$H$_{33}$ | C(CH$_3$)$_2$—CH$_2$—O | OH |
| 221. | n-C$_{16}$H$_{33}$ | CH$_2$C(CH$_3$)$_2$—O | H |
| 222. | n-C$_{16}$H$_{33}$ | CH$_2$C(CH$_3$)$_2$—O | OH |
| 223. | n-C$_{16}$H$_{33}$ | CH$_2$—CH(C$_2$H$_5$)—O | H |
| 224. | n-C$_{16}$H$_{33}$ | CH$_2$—CH(C$_2$H$_5$)—O | OH |
| 225. | iso-C$_3$H$_7$ | CH$_2$—CH$_2$—O | H |
| 226. | iso-C$_3$H$_7$ | CH$_2$—CH$_2$—O | OH |
| 227. | iso-C$_3$H$_7$ | CH(CH$_3$)—CH$_2$—O | H |
| 228. | iso-C$_3$H$_7$ | CH(CH$_3$)—CH$_2$—O | OH |
| 229. | iso-C$_3$H$_7$ | CH$_2$—CH(CH$_3$)—O | H |
| 230. | iso-C$_3$H$_7$ | CH$_2$—CH(CH$_3$)—O | OH |
| 231. | iso-C$_3$H$_7$ | CH(C$_2$H$_5$)—CH$_2$—O | H |
| 232. | iso-C$_3$H$_7$ | CH(C$_2$H$_5$)—CH$_2$—O | OH |
| 233. | iso-C$_3$H$_7$ | C(CH$_3$)$_2$—CH$_2$—O | H |
| 234. | iso-C$_3$H$_7$ | C(CH$_3$)$_2$—CH$_2$—O | OH |
| 235. | iso-C$_3$H$_7$ | CH$_2$C(CH$_3$)$_2$—O | H |
| 236. | iso-C$_3$H$_7$ | CH$_2$C(CH$_3$)$_2$—O | OH |
| 237. | iso-C$_3$H$_7$ | CH$_2$—CH(C$_2$H$_5$)—O | H |
| 238. | iso-C$_3$H$_7$ | CH$_2$—CH(C$_2$H$_5$)—O | OH |
| 239. | iso-C$_4$H$_9$ | CH$_2$—CH$_2$—O | H |
| 240. | iso-C$_4$H$_9$ | CH$_2$—CH$_2$—O | OH |
| 241. | iso-C$_4$H$_9$ | CH(CH$_3$)—CH$_2$—O | H |
| 242. | iso-C$_4$H$_9$ | CH(CH$_3$)—CH$_2$—O | OH |
| 243. | iso-C$_4$H$_9$ | CH$_2$—CH(CH$_3$)—O | H |
| 244. | iso-C$_4$H$_9$ | CH$_2$—CH(CH$_3$)—O | OH |
| 245. | iso-C$_4$H$_9$ | CH(C$_2$H$_5$)—CH$_2$—O | H |
| 246. | iso-C$_4$H$_9$ | CH(C$_2$H$_5$)—CH$_2$—O | OH |
| 247. | iso-C$_4$H$_9$ | C(CH$_3$)$_2$—CH$_2$—O | H |
| 248. | iso-C$_4$H$_9$ | C(CH$_3$)$_2$—CH$_2$—O | OH |
| 249. | iso-C$_4$H$_9$ | CH$_2$C(CH$_3$)$_2$—O | H |
| 250. | iso-C$_4$H$_9$ | CH$_2$C(CH$_3$)$_2$—O | OH |
| 251. | iso-C$_4$H$_9$ | CH$_2$—CH(C$_2$H$_5$)—O | H |
| 252. | iso-C$_4$H$_9$ | CH$_2$—CH(C$_2$H$_5$)—O | OH |
| 253. | iso-C$_5$H$_{11}$ | CH$_2$—CH$_2$—O | H |
| 254. | iso-C$_5$H$_{11}$ | CH$_2$—CH$_2$—O | OH |
| 255. | iso-C$_5$H$_{11}$ | CH(CH$_3$)—CH$_2$—O | H |
| 256. | iso-C$_5$H$_{11}$ | CH(CH$_3$)—CH$_2$—O | OH |
| 257. | iso-C$_5$H$_{11}$ | CH$_2$—CH(CH$_3$)—O | H |
| 258. | iso-C$_5$H$_{11}$ | CH$_2$—CH(CH$_3$)—O | OH |
| 259. | iso-C$_5$H$_{11}$ | CH(C$_2$H$_5$)—CH$_2$—O | H |
| 260. | iso-C$_5$H$_{11}$ | CH(C$_2$H$_5$)—CH$_2$—O | OH |
| 261. | iso-C$_5$H$_{11}$ | C(CH$_3$)$_2$—CH$_2$—O | H |
| 262. | iso-C$_5$H$_{11}$ | C(CH$_3$)$_2$—CH$_2$—O | OH |
| 263. | iso-C$_5$H$_{11}$ | CH$_2$C(CH$_3$)$_2$—O | H |
| 264. | iso-C$_5$H$_{11}$ | CH$_2$C(CH$_3$)$_2$—O | OH |
| 265. | iso-C$_5$H$_{11}$ | CH$_2$—CH(C$_2$H$_5$)—O | H |
| 266. | iso-C$_5$H$_{11}$ | CH$_2$—CH(C$_2$H$_5$)—O | OH |
| 267. | iso-C$_6$H$_{13}$ | CH$_2$—CH$_2$—O | H |
| 268. | iso-C$_6$H$_{13}$ | CH$_2$—CH$_2$—O | OH |
| 269. | iso-C$_6$H$_{13}$ | CH(CH$_3$)—CH$_2$—O | H |
| 270. | iso-C$_6$H$_{13}$ | CH(CH$_3$)—CH$_2$—O | OH |
| 271. | iso-C$_6$H$_{13}$ | CH$_2$—CH(CH$_3$)—O | H |
| 272. | iso-C$_6$H$_{13}$ | CH$_2$—CH(CH$_3$)—O | OH |
| 273. | iso-C$_6$H$_{13}$ | CH(C$_2$H$_5$)—CH$_2$—O | H |
| 274. | iso-C$_6$H$_{13}$ | CH(C$_2$H$_5$)—CH$_2$—O | OH |
| 275. | iso-C$_6$H$_{13}$ | C(CH$_3$)$_2$—CH$_2$—O | H |
| 276. | iso-C$_6$H$_{13}$ | C(CH$_3$)$_2$—CH$_2$—O | OH |
| 277. | iso-C$_6$H$_{13}$ | CH$_2$C(CH$_3$)$_2$—O | H |
| 278. | iso-C$_6$H$_{13}$ | CH$_2$C(CH$_3$)$_2$—O | OH |
| 279. | iso-C$_6$H$_{13}$ | CH$_2$—CH(C$_2$H$_5$)—O | H |
| 280. | iso-C$_6$H$_{13}$ | CH$_2$—CH(C$_2$H$_5$)—O | OH |
| 281. | iso-C$_7$H$_{15}$ | CH$_2$—CH$_2$—O | H |
| 282. | iso-C$_7$H$_{15}$ | CH$_2$—CH$_2$—O | OH |
| 283. | iso-C$_7$H$_{15}$ | CH(CH$_3$)—CH$_2$—O | H |
| 284. | iso-C$_7$H$_{15}$ | CH(CH$_3$)—CH$_2$—O | OH |
| 285. | iso-C$_7$H$_{15}$ | CH$_2$—CH(CH$_3$)—O | H |
| 286. | iso-C$_7$H$_{15}$ | CH$_2$—CH(CH$_3$)—O | OH |
| 287. | iso-C$_7$H$_{15}$ | CH(C$_2$H$_5$)—CH$_2$—O | H |
| 288. | iso-C$_7$H$_{15}$ | CH(C$_2$H$_5$)—CH$_2$—O | OH |
| 289. | iso-C$_7$H$_{15}$ | C(CH$_3$)$_2$—CH$_2$—O | H |
| 290. | iso-C$_7$H$_{15}$ | C(CH$_3$)$_2$—CH$_2$—O | OH |
| 291. | iso-C$_7$H$_{15}$ | CH$_2$C(CH$_3$)$_2$—O | H |
| 292. | iso-C$_7$H$_{15}$ | CH$_2$C(CH$_3$)$_2$—O | OH |
| 293. | iso-C$_7$H$_{15}$ | CH$_2$—CH(C$_2$H$_5$)—O | H |
| 294. | iso-C$_7$H$_{15}$ | CH$_2$—CH(C$_2$H$_5$)—O | OH |
| 295. | iso-C$_8$H$_{17}$ | CH$_2$—CH$_2$—O | H |
| 296. | iso-C$_8$H$_{17}$ | CH$_2$—CH$_2$—O | OH |
| 297. | iso-C$_8$H$_{17}$ | CH(CH$_3$)—CH$_2$—O | H |
| 298. | iso-C$_8$H$_{17}$ | CH(CH$_3$)—CH$_2$—O | OH |
| 299. | iso-C$_8$H$_{17}$ | CH$_2$—CH(CH$_3$)—O | H |
| 300. | iso-C$_8$H$_{17}$ | CH$_2$—CH(CH$_3$)—O | OH |
| 301. | iso-C$_8$H$_{17}$ | CH(C$_2$H$_5$)—CH$_2$—O | H |
| 302. | iso-C$_8$H$_{17}$ | CH(C$_2$H$_5$)—CH$_2$ O | OH |
| 303. | iso-C$_8$H$_{17}$ | C(CH$_3$)$_2$—CH$_2$—O | H |
| 304. | iso-C$_8$H$_{17}$ | C(CH$_3$)$_2$—CH$_2$—O | OH |
| 305. | iso-C$_8$H$_{17}$ | CH$_2$C(CH$_3$)$_2$—O | H |
| 306. | iso-C$_8$H$_{17}$ | CH$_2$C(CH$_3$)$_2$—O | OH |
| 307. | iso-C$_8$H$_{17}$ | CH$_2$—CH(C$_2$H$_5$)—O | H |
| 308. | iso-C$_8$H$_{17}$ | CH$_2$—CH(C$_2$H$_5$)—O | OH |
| 309. | iso-C$_9$H$_{19}$ | CH$_2$—CH$_2$—O | H |
| 310. | iso-C$_9$H$_{19}$ | CH$_2$—CH$_2$—O | OH |
| 311. | iso-C$_9$H$_{19}$ | CH(CH$_3$)—CH$_2$—O | H |
| 312. | iso-C$_9$H$_{19}$ | CH(CH$_3$)—CH$_2$—O | OH |
| 313. | iso-C$_9$H$_{19}$ | CH$_2$—CH(CH$_3$)—O | H |
| 314. | iso-C$_9$H$_{19}$ | CH$_2$—CH(CH$_3$)—O | OH |
| 315. | iso-C$_9$H$_{19}$ | CH(C$_2$H$_5$)—CH$_2$—O | H |
| 316. | iso-C$_9$H$_{19}$ | CH(C$_2$H$_5$)—CH$_2$—O | OH |
| 317. | iso-C$_9$H$_{19}$ | C(CH$_3$)$_2$—CH$_2$—O | H |
| 318. | iso-C$_9$H$_{19}$ | C(CH$_3$)$_2$—CH$_2$—O | OF |
| 319. | iso-C$_9$H$_{19}$ | CH$_2$C(CH$_3$)$_2$—O | H |

TABLE-A-continued

| row | R₂ | AO | R |
|---|---|---|---|
| 320. | iso-$C_9H_{19}$ | $CH_2C(CH_3)_2$—O | OH |
| 321. | iso-$C_9H_{19}$ | $CH_2$—$CH(C_2H_5)$—O | H |
| 322. | iso-$C_9H_{19}$ | $CH_2$—$CH(C_2H_5)$—O | OH |
| 323. | iso-$C_{10}H_{21}$ | $CH_2$—$CH_2$—O | H |
| 324. | iso-$C_{10}H_{21}$ | $CH_2$—$CH_2$—O | OH |
| 325. | iso-$C_{10}H_{21}$ | $CH(CH_3)$—$CH_2$—O | H |
| 326. | iso-$C_{10}H_{21}$ | $CH(CH_3)$—$CH_2$—O | OH |
| 327. | iso-$C_{10}H_{21}$ | $CH_2$—$CH(CH_3)$—O | H |
| 328. | iso-$C_{10}H_{21}$ | $CH_2$—$CH(CH_3)$—O | OH |
| 329. | iso-$C_{10}H_{21}$ | $CH(C_2H_5)$—$CH_2$—O | H |
| 330. | iso-$C_{10}H_{21}$ | $CH(C_2H_5)$—$CH_2$—O | OH |
| 331. | iso-$C_{10}H_{21}$ | $C(CH_3)_2$—$CH_2$—O | H |
| 332. | iso-$C_{10}H_{21}$ | $C(CH_3)_2$—$CH_2$—O | OH |
| 333. | iso-$C_{10}H_{21}$ | $CH_2C(CH_3)_2$—O | H |
| 334. | iso-$C_{10}H_{21}$ | $CH_2C(CH_3)_2$—O | OH |
| 335. | iso-$C_{10}H_{21}$ | $CH_2$—$CH(C_2H_5)$—O | H |
| 336. | iso-$C_{10}H_{21}$ | $CH_2$—$CH(C_2H_5)$—O | OH |
| 337. | iso-$C_{11}H_{23}$ | $CH_2$—$CH_2$—O | H |
| 338. | iso-$C_{11}H_{23}$ | $CH_2$—$CH_2$—O | OH |
| 339. | iso-$C_{11}H_{23}$ | $CH(CH_3)$—$CH_2$—O | H |
| 340. | iso-$C_{11}H_{23}$ | $CH(CH_3)$—$CH_2$—O | OH |
| 341. | iso-$C_{11}H_{23}$ | $CH_2$—$CH(CH_3)$—O | H |
| 342. | iso-$C_{11}H_{23}$ | $CH_2$—$CH(CH_3)$—O | OH |
| 343. | iso-$C_{11}H_{23}$ | $CH(C_2H_5)$—$CH_2$—O | H |
| 344. | iso-$C_{11}H_{23}$ | $CH(C_2H_5)$—$CH_2$—O | OH |
| 345. | iso-$C_{11}H_{23}$ | $C(CH_3)_2$—$CH_2$—O | H |
| 346. | iso-$C_{11}H_{23}$ | $C(CH_3)_2$—$CH_2$—O | OH |
| 347. | iso-$C_{11}H_{23}$ | $CH_2C(CH_3)_2$—O | H |
| 348. | iso-$C_{11}H_{23}$ | $CH_2C(CH_3)_2$—O | OH |
| 349. | iso-$C_{11}H_{23}$ | $CH_2$—$CH(C_2H_5)$—O | H |
| 350. | iso-$C_{11}H_{23}$ | $CH_2$—$CH(C_2H_5)$—O | OH |
| 351. | iso-$C_{12}H_{25}$ | $CH_2$—$CH_2$—O | H |
| 352. | iso-$C_{12}H_{25}$ | $CH_2$—$CH_2$—O | OH |
| 353. | iso-$C_{12}H_{25}$ | $CH(CH_3)$—$CH_2$—O | H |
| 354. | iso-$C_{12}H_{25}$ | $CH(CH_3)$—$CH_2$—O | OH |
| 355. | iso-$C_{12}H_{25}$ | $CH_2$—$CH(CH_3)$—O | H |
| 356. | iso-$C_{12}H_{25}$ | $CH_2$—$CH(CH_3)$—O | OH |
| 357. | iso-$C_{12}H_{25}$ | $CH(C_2H_5)$—$CH_2$—O | H |
| 358. | iso-$C_{12}H_{25}$ | $CH(C_2H_5)$—$CH_2$—O | OH |
| 359. | iso-$C_{12}H_{25}$ | $C(CH_3)_2$—$CH_2$—O | H |
| 360. | iso-$C_{12}H_{25}$ | $C(CH_3)_2$—$CH_2$—O | OH |
| 361. | iso-$C_{12}H_{25}$ | $CH_2C(CH_3)_2$—O | H |
| 362. | iso-$C_{12}H_{25}$ | $CH_2C(CH_3)_2$—O | OH |
| 363. | iso-$C_{12}H_{25}$ | $CH_2$—$CH(C_2H_5)$—O | H |
| 364. | iso-$C_{12}H_{25}$ | $CH_2$—$CH(C_2H_5)$—O | OH |
| 365. | iso-$C_{13}H_{27}$ | $CH_2$—$CH_2$—O | H |
| 366. | iso-$C_{13}H_{27}$ | $CH_2$—$CH_2$—O | OH |
| 367. | iso-$C_{13}H_{27}$ | $CH(CH_3)$—$CH_2$—O | H |
| 368. | iso-$C_{13}H_{27}$ | $CH(CH_3)$—$CH_2$—O | OH |
| 369. | iso-$C_{13}H_{27}$ | $CH_2$—$CH(CH_3)$—O | H |
| 370. | iso-$C_{13}H_{27}$ | $CH_2$—$CH(CH_3)$—O | OH |
| 371. | iso-$C_{13}H_{27}$ | $CH(C_2H_5)$—$CH_2$—O | H |
| 372. | iso-$C_{13}H_{27}$ | $CH(C_2H_5)$—$CH_2$—O | OH |
| 373. | iso-$C_{13}H_{27}$ | $C(CH_3)_2$—$CH_2$—O | H |
| 374. | iso-$C_{13}H_{27}$ | $C(CH_3)_2$—$CH_2$—O | OH |
| 375. | iso-$C_{13}H_{27}$ | $CH_2C(CH_3)_2$—O | H |
| 376. | iso-$C_{13}H_{27}$ | $CH_2C(CH_3)_2$—O | OH |
| 377. | iso-$C_{13}H_{27}$ | $CH_2$—$CH(C_2H_5)$—O | H |
| 378. | iso-$C_{13}H_{27}$ | $CH_2$—$CH(C_2H_5)$—O | OH |
| 379. | iso-$C_{14}H_{29}$ | $CH_2$—$CH_2$—O | H |
| 380. | iso-$C_{14}H_{29}$ | $CH_2$—$CH_2$—O | OH |
| 381. | iso-$C_{14}H_{29}$ | $CH(CH_3)$—$CH_2$—O | H |
| 382. | iso-$C_{14}H_{29}$ | $CH(CH_3)$—$CH_2$—O | OH |
| 383. | iso-$C_{14}H_{29}$ | $CH_2$—$CH(CH_3)$—O | H |
| 384. | iso-$C_{14}H_{29}$ | $CH_2$—$CH(CH_3)$—O | OH |
| 385. | iso-$C_{14}H_{29}$ | $CH(C_2H_5)$—$CH_2$—O | H |
| 386. | iso-$C_{14}H_{29}$ | $CH(C_2H_5)$—$CH$—O | OH |
| 387. | iso-$C_{14}H_{29}$ | $C(CH_3)_2$—$CH_2$—O | H |
| 388. | iso-$C_{14}H_{29}$ | $C(CH_3)_2$—$CH_2$—O | OH |
| 389. | iso-$C_{14}H_{29}$ | $CH_2C(CH_3)_2$—O | H |
| 390. | iso-$C_{14}H_{29}$ | $CH_2C(CH_3)_2$—O | OH |
| 391. | iso-$C_{14}H_{29}$ | $CH_2$—$CH(C_2H_5)$—O | H |
| 392. | iso-$C_{14}H_{29}$ | $CH_2$—$CH(C_2H_5)$—O | OH |
| 393. | iso-$C_{15}H_{31}$ | $CH_2$—$CH_2$—O | H |
| 394. | iso-$C_{15}H_{31}$ | $CH_2$—$CH_2$—O | OH |
| 395. | iso-$C_{15}H_{31}$ | $CH(CH_3)$—$CH_2$—O | H |
| 396. | iso-$C_{15}H_{31}$ | $CH(CH_3)$—$CH_2$—O | OF |
| 397. | iso-$C_{15}H_{31}$ | $CH_2$—$CH(CH_3)$—O | H |
| 398. | iso-$C_{15}H_{31}$ | $CH_2$—$CH(CH_3)$—O | OH |
| 399. | iso-$C_{15}H_{31}$ | $CH(C_2H_5)$—$CH_2$—O | H |
| 400. | iso-$C_{15}H_{31}$ | $CH(C_2H_5)$—$CH_2$—O | OH |
| 401. | iso-$C_{15}H_{31}$ | $C(CH_3)_2$—$CH_2$—O | H |
| 402. | iso-$C_{15}H_{31}$ | $C(CH_3)_2$—$CH_2$—O | OH |
| 403. | iso-$C_{15}H_{31}$ | $CH_2C(CH_3)_2$—O | H |
| 404. | iso-$C_{15}H_{31}$ | $CH_2C(CH_3)_2$—O | OH |
| 405. | iso-$C_{15}H_{31}$ | $CH_2$—$CH(C_2H_5)$—O | H |
| 406. | iso-$C_{15}H_{31}$ | $CH_2$—$CH(C_2H_5)$—O | OH |
| 407. | iso-$C_{16}H_{33}$ | $CH_2$—$CH_2$—O | H |
| 408. | iso-$C_{16}H_{33}$ | $CH_2$—$CH_2$—O | OH |
| 409. | iso-$C_{16}H_{33}$ | $CH(CH_3)$—$CH_2$—O | H |
| 410. | iso-$C_{16}H_{33}$ | $CH(CH_3)$—$CH_2$—O | OH |
| 411. | iso-$C_{16}H_{33}$ | $CH_2$—$CH(CH_3)$—O | H |
| 412. | iso-$C_{16}H_{33}$ | $CH_2$—$CH(CH_3)$—O | OH |
| 413. | iso-$C_{16}H_{33}$ | $CH(C_2H_5)$—$CH_2$—O | H |
| 414. | iso-$C_{16}H_{33}$ | $CH(C_2H_5)$—$CH_2$—O | OH |
| 415. | iso-$C_{16}H_{33}$ | $C(CH_3)_2$—$CH_2$—O | H |
| 416. | iso-$C_{16}H_{33}$ | $C(CH_3)_2$—$CH_2$—O | OH |
| 417. | iso-$C_{16}H_{33}$ | $CH_2C(CH_3)_2$—O | H |
| 418. | iso-$C_{16}H_{33}$ | $CH_2C(CH_3)_2$—O | OH |
| 419. | iso-$C_{16}H_{33}$ | $CH_2$—$CH(C_2H_5)$—O | H |
| 420. | iso-$C_{16}H_{33}$ | $CH_2$—$CH(C_2H_5)$—O | OH |

In an alternate embodiment, the at least one compound of general formula (I) is

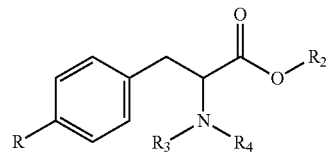

wherein

R denotes H, OH or $OR_5$, wherein $R_5$ is $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

and $R_2$ denotes $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

$R_3$ denotes H;

$R_4$ denotes —C(=O)$R_1$ wherein $R_1$ is linear or branched, unsubstituted $C_2$-$C_{16}$ alkyl.

Preferably $R_2$ is $(AO)_n$—H wherein (AO) is independently $CH_2$—$CH_2$—O, $CH(CH_3)$—$CH_2$—O or $CH_2$—$CH(CH_3)$—O and more preferably (AO) is $CH_2$—$CH_2$—O.

In a preferred embodiment, n is an integer in the range of 1 to 38 or 1 to 37 or 1 to 36 or 1 to 35 or 1 to 34 or 1 to 35 or 1 to 34 or 1 to 33 or 1 to 32 or 1 to 31 or 1 to 30 or 2 to 38 or 2 to 37 or 2 to 36 or 2 to 35 or 2 to 34 or 2 to 35 or 2 to 34 or 2 to 33 or 2 to 32 or 2 to 31 or 2 to 30 or 3 to 38 more preferably in the range of 4 to 37 or 5 to 37 or even more preferably in the range of 5 to 36 or 5 to 35 or 5 to 34 or 6 to 36 or 6 to 35 or 6 to 34 or 7 to 36 or 7 to 35 or 7 to 34 still more preferably in the range of 8 to 33 or 8 to 32 or 8 to 31 or 8 to 30 or 9 to 33 or 9 to 32 or 9 to 31 or 9 to 30 and most preferably in the range of 9 to 28 or 9 to 26 or 9 to 24 or 9 to 22 or 9 to 20 or 9 to 18 or 9 to 16 or 9 to 14 or 9 to 12 or 10 to 30 or 10 to 28 or 10 to 26 or 10 to 24 or 10 to 22 or 10 to 20 or 10 to 18 or 10 to 16.

Preferably, $R_4$ is —C(=O)$R_1$, wherein $R_1$ is selected from the group of ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, isotetradecyl, isopentadecyl and isohexadecyl.

More preferably, $R_4$ is —C(=O)$R_1$, wherein $R_1$ is selected from the group of ethyl, n-propyl, n-butyl, n-hexyl, n-decyl, n-dodecyl, n-tetradecyl, isopropyl, isobutyl, isohexyl, isododecyl and iso-tetradecyl.

Preferably, the at least one compound of general formula (I) is a compound of general formula (Ib)

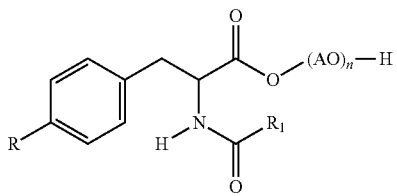

(Ib)

wherein
R denotes H or OH;
$R_1$ denotes linear or branched, unsubstituted $C_2$-$C_{16}$ alkyl;
(AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and
n is an integer in the range from 1 to 39;
Particularly preferably, compounds of general formula (Ib) are compounds as defined in Table 40 to Table 78.

Table-40
Compound of general formula (Ib) wherein n=1 and combination of variables $R_1$, AO and R correspond to each row of Table B Table-41
Compound of general formula (Ib) wherein n=2 and combination of variables $R_1$, AO and R correspond to each row of Table B Table-42
Compound of general formula (Ib) wherein n=3 and combination of variables $R_1$, AO and R correspond to each row of Table B Table-43
Compound of general formula (Ib) wherein n=4 and combination of variables $R_1$, AO and R correspond to each row of Table B Table-44
Compound of general formula (Ib) wherein n=5 and combination of variables $R_1$, AO and R correspond to each row of Table B Table-45
Compound of general formula (Ib) wherein n=6 and combination of variables $R_1$, AO and R correspond to each row of Table B Table-46
Compound of general formula (Ib) wherein n=7 and combination of variables $R_1$, AO and R correspond to each row of Table B Table-47
Compound of general formula (Ib) wherein n=8 and combination of variables $R_1$, AO and R correspond to each row of Table B Table-48
Compound of general formula (Ib) wherein n=9 and combination of variables $R_1$, AO and R correspond to each row of Table B Table-49
Compound of general formula (Ib) wherein n=10 and combination of variables $R_1$, AO and R correspond to each row of Table B Table-50
Compound of general formula (Ib) wherein n=11 and combination of variables $R_1$, AO and R correspond to each row of Table B Table-51
Compound of general formula (Ib) wherein n=12 and combination of variables $R_1$, AO and R correspond to each row of Table B Table-52
Compound of general formula (Ib) wherein n=13 and combination of variables $R_1$, AO and R correspond to each row of Table B Table-53
Compound of general formula (Ib) wherein n=14 and combination of variables $R_1$, AO and R correspond to each row of Table B Table-54
Compound of general formula (Ib) wherein n=15 and combination of variables $R_1$, AO and R correspond to each row of Table B Table-55
Compound of general formula (Ib) wherein n=16 and combination of variables $R_1$, AO and R correspond to each row of Table B Table-56
Compound of general formula (Ib) wherein n=17 and combination of variables $R_1$, AO and R correspond to each row of Table B Table-57
Compound of general formula (Ib) wherein n=18 and combination of variables $R_1$, AO and R correspond to each row of Table B Table-58
Compound of general formula (Ib) wherein n=19 and combination of variables $R_1$, AO and R correspond to each row of Table B Table-59
Compound of general formula (Ib) wherein n=20 and combination of variables $R_1$, AO and R correspond to each row of Table B Table-60
Compound of general formula (Ib) wherein n=21 and combination of variables $R_1$, AO and R correspond to each row of Table B Table-61
Compound of general formula (Ib) wherein n=22 and combination of variables $R_1$, AO and R correspond to each row of Table B Table-62
Compound of general formula (Ib) wherein n=23 and combination of variables $R_1$, AO and R correspond to each row of Table B Table-63
Compound of general formula (Ib) wherein n=24 and combination of variables R₁, AO and R correspond to each row of Table B Table-64
Compound of general formula (Ib) wherein n=25 and combination of variables R₁, AO and R correspond to each row of Table B Table-65
Compound of general formula (Ib) wherein n=26 and combination of variables R₁, AO and R correspond to each row of Table B Table-66
Compound of general formula (Ib) wherein n=27 and combination of variables R₁, AO and R correspond to each row of Table B Table-67
Compound of general formula (Ib) wherein n=28 and combination of variables R₁, AO and R correspond to each row of Table B Table-68
Compound of general formula (Ib) wherein n=29 and combination of variables R₁, AO and R correspond to each row of Table B Table-69
Compound of general formula (Ib) wherein n=30 and combination of variables R₁, AO and R correspond to each row of Table B Table-70
Compound of general formula (Ib) wherein n=31 and combination of variables R₁, AO and R correspond to each row of Table B Table-71
Compound of general formula (Ib) wherein n=32 and combination of variables R₁, AO and R correspond to each row of Table B Table-72
Compound of general formula (Ib) wherein n=33 and combination of variables R₁, AO and R correspond to each row of Table B Table-73
Compound of general formula (Ib) wherein n=34 and combination of variables R₁, AO and R correspond to each row of Table B Table-74
Compound of general formula (Ib) wherein n=35 and combination of variables R₁, AO and R correspond to each row of Table B Table-75
Compound of general formula (Ib) wherein n=36 and combination of variables R₁, AO and R correspond to each row of Table B Table-76
Compound of general formula (Ib) wherein n=37 and combination of variables R₁, AO and R correspond to each row of Table B Table-77
Compound of general formula (Ib) wherein n=38 and combination of variables R₁, AO and R correspond to each row of Table B Table-78
Compound of general formula (Ib) wherein n=39 and combination of variables R₁, AO and R correspond to each row of Table B

TABLE B

| row | R₁ | AO | R |
|---|---|---|---|
| 421. | $C_2H_5$ | $CH_2-CH_2-O$ | H |
| 422. | $C_2H_5$ | $CH_2-CH_2-O$ | OH |
| 423. | $C_2H_5$ | $CH(CH_3)-CH_2-O$ | H |
| 424. | $C_2H_5$ | $CH(CH_3)-CH_2-O$ | OH |
| 425. | $C_2H_5$ | $CH_2-CH(CH_3)-O$ | H |
| 426. | $C_2H_5$ | $CH_2-CH(CH_3)-O$ | OH |
| 427. | $C_2H_5$ | $CH(C_2H_5)-CH_2-O$ | H |
| 428. | $C_2H_5$ | $CH(C_2H_5)-CH_2-O$ | OH |
| 429. | $C_2H_5$ | $C(CH_3)_2-CH_2-O$ | H |
| 430. | $C_2H_5$ | $C(CH_3)_2-CH_2-O$ | OH |
| 431. | $C_2H_5$ | $CH_2C(CH_3)_2-O$ | H |
| 432. | $C_2H_5$ | $CH_2C(CH_3)_2-O$ | OH |
| 433. | $C_2H_5$ | $CH_2-CH(C_2H_5)-O$ | H |
| 434. | $C_2H_5$ | $CH_2-CH(C_2H_5)-O$ | OH |
| 435. | $n-C_3H_7$ | $CH_2-CH_2-O$ | H |
| 436. | $n-C_3H_7$ | $CH_2-CH_2-O$ | OH |
| 437. | $n-C_3H_7$ | $CH(CH_3)-CH_2-O$ | H |
| 438. | $n-C_3H_7$ | $CH(CH_3)-CH_2-O$ | OH |
| 439. | $n-C_3H_7$ | $CH_2-CH(CH_3)-O$ | H |
| 440. | $n-C_3H_7$ | $CH_2-CH(CH_3)-O$ | OH |
| 441. | $n-C_3H_7$ | $CH(C_2H_5)-CH_2-O$ | H |
| 442. | $n-C_3H_7$ | $CH(C_2H_5)-CH_2-O$ | OH |
| 443. | $n-C_3H_7$ | $C(CH_3)_2-CH_2-O$ | H |
| 444. | $n-C_3H_7$ | $C(CH_3)_2-CH_2-O$ | OH |
| 445. | $n-C_3H_7$ | $CH_2C(CH_3)_2-O$ | H |
| 446. | $n-C_3H_7$ | $CH_2C(CH_3)_2-O$ | OH |
| 447. | $n-C_3H_7$ | $CH_2-CH(C_2H_5)-O$ | H |
| 448. | $n-C_3H_7$ | $CH_2-CH(C_2H_5)-O$ | OH |
| 449. | $n-C_4H_9$ | $CH_2-CH_2-O$ | H |
| 450. | $n-C_4H_9$ | $CH_2-CH_2-O$ | OH |
| 451. | $n-C_4H_9$ | $CH(CH_3)-CH_2-O$ | H |
| 452. | $n-C_4H_9$ | $CH(CH_3)-CH_2-O$ | OH |
| 453. | $n-C_4H_9$ | $CH_2-CH(CH_3)-O$ | H |
| 454. | $n-C_4H_9$ | $CH_2-CH(CH_3)-O$ | OH |
| 455. | $n-C_4H_9$ | $CH(C_2H_5)-CH_2-O$ | H |
| 456. | $n-C_4H_9$ | $CH(C_2H_5)-CH_2-O$ | OH |
| 457. | $n-C_4H_9$ | $C(CH_3)_2-CH_2-O$ | H |
| 458. | $n-C_4H_9$ | $C(CH_3)_2-CH_2-O$ | OH |
| 459. | $n-C_4H_9$ | $CH_2C(CH_3)_2-O$ | H |
| 460. | $n-C_4H_9$ | $CH_2C(CH_3)_2-O$ | OH |
| 461. | $n-C_4H_9$ | $CH_2-CH(C_2H_5)-O$ | H |
| 462. | $n-C_4H_9$ | $CH_2-CH(C_2H_5)-O$ | OH |
| 463. | $n-C_5H_{11}$ | $CH_2-CH_2-O$ | H |
| 464. | $n-C_5H_{11}$ | $CH_2-CH_2-O$ | OH |
| 465. | $n-C_5H_{11}$ | $CH(CH_3)-CH_2-O$ | H |
| 466. | $n-C_5H_{11}$ | $CH(CH_3)-CH_2-O$ | OH |
| 467. | $n-C_5H_{11}$ | $CH_2-CH(CH_3)-O$ | H |
| 468. | $n-C_5H_{11}$ | $CH_2-CH(CH_3)-O$ | OH |
| 469. | $n-C_5H_{11}$ | $CH(C_2H_5)-CH_2-O$ | H |
| 470. | $n-C_5H_{11}$ | $CH(C_2H_5)-CH_2-O$ | OH |
| 471. | $n-C_5H_{11}$ | $C(CH_3)_2-CH_2-O$ | H |
| 472. | $n-C_5H_{11}$ | $C(CH_3)_2-CH_2-O$ | OH |
| 473. | $n-C_5H_{11}$ | $CH_2C(CH_3)_2-O$ | H |
| 474. | $n-C_5H_{11}$ | $CH_2C(CH_3)_2-O$ | OH |
| 475. | $n-C_5H_{11}$ | $CH_2-CH(C_2H_5)-O$ | H |
| 476. | $n-C_5H_{11}$ | $CH_2-CH(C_2H_5)-O$ | OH |
| 477. | $n-C_6H_{13}$ | $CH_2-CH_2-O$ | H |
| 478. | $n-C_6H_{13}$ | $CH_2-CH_2-O$ | OH |
| 479. | $n-C_6H_{13}$ | $CH(CH_3)-CH_2-O$ | H |
| 480. | $n-C_6H_{13}$ | $CH(CH_3)-CH_2-O$ | OH |
| 481. | $n-C_6H_{13}$ | $CH_2-CH(CH_3)-O$ | H |
| 482. | $n-C_6H_{13}$ | $CH_2-CH(CH_3)-O$ | OH |
| 483. | $n-C_6H_{13}$ | $CH(C_2H_5)-CH_2-O$ | H |
| 484. | $n-C_6H_{13}$ | $CH(C_2H_5)-CH_2-O$ | OH |
| 485. | $n-C_6H_{13}$ | $C(CH_3)_2-CH_2-O$ | H |
| 486. | $n-C_6H_{13}$ | $C(CH_3)_2-CH_2-O$ | OH |
| 487. | $n-C_6H_{13}$ | $CH_2C(CH_3)_2-O$ | H |
| 488. | $n-C_6H_{13}$ | $CH_2C(CH_3)_2-O$ | OH |
| 489. | $n-C_6H_{13}$ | $CH_2-CH(C_2H_5)-O$ | H |
| 490. | $n-C_6H_{13}$ | $CH_2-CH(C_2H_5)-O$ | OH |
| 491. | $n-C_7H_{15}$ | $CH_2-CH_2-O$ | H |
| 492. | $n-C_7H_{15}$ | $CH_2-CH_2-O$ | OH |
| 493. | $n-C_7H_{15}$ | $CH(CH_3)-CH_2-O$ | H |
| 494. | $n-C_7H_{15}$ | $CH(CH_3)-CH_2-O$ | OH |
| 495. | $n-C_7H_{15}$ | $CH_2-CH(CH_3)-O$ | H |
| 496. | $n-C_7H_{15}$ | $CH_2-CH(CH_3)-O$ | OH |
| 497. | $n-C_7H_{15}$ | $CH(C_2H_5)-CH_2-O$ | H |
| 498. | $n-C_7H_{15}$ | $CH(C_2H_5)-CH_2-O$ | OH |

TABLE B-continued

| row | $R_1$ | AO | R |
|---|---|---|---|
| 499. | n-$C_7H_{15}$ | $C(CH_3)_2$—$CH_2$—O | H |
| 500. | n-$C_7H_{15}$ | $C(CH_3)_2$—$CH_2$—O | OH |
| 501. | n-$C_7H_{15}$ | $CH_2C(CH_3)_2$—O | H |
| 502. | n-$C_7H_{15}$ | $CH_2C(CH_3)_2$—O | OH |
| 503 | n-$C_7H_{15}$ | $CH_2$—$CH(C_2H_5)$—O | H |
| 504. | n-$C_7H_{15}$ | $CH_2$—$CH(C_2H_5)$—O | OH |
| 505. | n-$C_8H_{17}$ | $CH_2$—$CH_2$—O | H |
| 506. | n-$C_8H_{17}$ | $CH_2$—$CH_2$—O | OH |
| 507. | n-$C_8H_{17}$ | $CH(CH_3)$—$CH_2$—O | H |
| 508. | n-$C_8H_{17}$ | $CH(CH_3)$—$CH_2$—O | OH |
| 509. | n-$C_8H_{17}$ | $CH_2$—$CH(CH_3)$—O | H |
| 510. | n-$C_8H_{17}$ | $CH_2$—$CH(CH_3)$—O | OH |
| 511. | n-$C_8H_{17}$ | $CH(C_2H_5)$—$CH_2$—O | H |
| 512. | n-$C_8H_{17}$ | $CH(C_2H_5)$—$CH_2$—O | OH |
| 513. | n-$C_8H_{17}$ | $C(CH_3)_2$—$CH_2$—O | H |
| 514. | n-$C_8H_{17}$ | $C(CH_3)_2$—$CH_2$—O | OH |
| 515. | n-$C_8H_{17}$ | $CH_2C(CH_3)_2$—O | H |
| 516. | n-$C_8H_{17}$ | $CH_2C(CH_3)_2$—O | OH |
| 517. | n-$C_8H_{17}$ | $CH_2$—$CH(C_2H_5)$—O | H |
| 518. | n-$C_8H_{17}$ | $CH_2$—$CH(C_2H_5)$—O | OH |
| 519. | n-$C_9H_{19}$ | $CH_2$—$CH_2$—O | H |
| 520. | n-$C_9H_{19}$ | $CH_2$—$CH_2$—O | OH |
| 521. | n-$C_9H_{19}$ | $CH(CH_3)$—$CH_2$—O | H |
| 522. | n-$C_9H_{19}$ | $CH(CH_3)$—$CH_2$—O | OH |
| 523. | n-$C_9H_{19}$ | $CH_2$—$CH(CH_3)$—O | H |
| 524. | n-$C_9H_{19}$ | $CH_2$—$CH(CH_3)$—O | OH |
| 525. | n-$C_9H_{19}$ | $CH(C_2H_5)$—$CH_2$—O | H |
| 526. | n-$C_9H_{19}$ | $CH(C_2H_5)$—$CH_2$—O | OH |
| 527. | n-$C_9H_{19}$ | $C(CH_3)_2$—$CH_2$—O | H |
| 528. | n-$C_9H_{19}$ | $C(CH_3)_2$—$CH_2$—O | OH |
| 529. | n-$C_9H_{19}$ | $CH_2C(CH_3)_2$—O | H |
| 530. | n-$C_9H_{19}$ | $CH_2C(CH_3)_2$—O | OH |
| 531. | n-$C_9H_{19}$ | $CH_2$—$CH(C_2H_5)$—O | H |
| 532. | n-$C_9H_{19}$ | $CH_2$—$CH(C_2H_5)$—O | OH |
| 533. | n-$C_{10}H_{21}$ | $CH_2$—$CH_2$—O | H |
| 534. | n-$C_{10}H_{21}$ | $CH_2$—$CH_2$—O | OH |
| 535. | n-$C_{10}H_{21}$ | $CH(CH_3)$—$CH_2$—O | H |
| 536. | n-$C_{10}H_{21}$ | $CH(CH_3)$—$CH_2$—O | OH |
| 537. | n-$C_{10}H_{21}$ | $CH_2$—$CH(CH_3)$—O | H |
| 538. | n-$C_{10}H_{21}$ | $CH_2$—$CH(CH_3)$—O | OH |
| 539. | n-$C_{10}H_{21}$ | $CH(C_2H_5)$—$CH_2$—O | H |
| 540. | n-$C_{10}H_{21}$ | $CH(C_2H_5)$—$CH_2$—O | OH |
| 541. | n-$C_{10}H_{21}$ | $C(CH_3)_2$—$CH_2$—O | H |
| 542. | n-$C_{10}H_{21}$ | $C(CH_3)_2$—$CH_2$—O | OH |
| 543. | n-$C_{10}H_{21}$ | $CH_2C(CH3)2$—O | H |
| 544. | n-$C_{10}H_{21}$ | $CH_2C(CH3)_2$—O | OH |
| 545. | n-$C_{10}H_{21}$ | $CH_2$—$CH(C_2H_5)$—O | H |
| 546. | n-$C_{10}H_{21}$ | $CH_2$—$CH(C_2H_5)$—O | OH |
| 547. | n-$C_{11}H_{23}$ | $CH_2$—$CH_2$—O | H |
| 548. | n-$C_{11}H_{23}$ | $CH_2$—$CH_2$—O | OH |
| 549. | n-$C_{11}H_{23}$ | $CH(CH_3)$—$CH_2$—O | H |
| 550. | n-$C_{11}H_{23}$ | $CH(CH_3)$—$CH_2$—O | OH |
| 551. | n-$C_{11}H_{23}$ | $CH_2$—$CH(CH_3)$—O | H |
| 552. | n-$C_{11}H_{23}$ | $CH_2$—$CH(CH_3)$—O | OH |
| 553. | n-$C_{11}H_{23}$ | $CH(C_2H_5)$—$CH_2$—O | H |
| 554. | n-$C_{11}H_{23}$ | $CH(C_2H_5)$—$CH_2$—O | OH |
| 555. | n-$C_{11}H_{23}$ | $C(CH_3)_2$—$CH_2$—O | H |
| 556. | n-$C_{11}H_{23}$ | $C(CH_3)_2$—$CH_2$—O | OH |
| 557. | n-$C_{11}H_{23}$ | $CH_2C(CH_3)_2$—O | H |
| 558. | n-$C_{11}H_{23}$ | $CH_2C(CH_3)_2$—O | OH |
| 559. | n-$C_{11}H_{23}$ | $CH_2$—$CH(C_2H_5)$—O | H |
| 560. | n-$C_{11}H_{23}$ | $CH_2$—$CH(C_2H_5)$—O | OH |
| 561. | n-$C_{12}H_{25}$ | $CH_2$—$CH_2$—O | H |
| 562. | n-$C_{12}H_{25}$ | $CH_2$—$CH_2$—O | OH |
| 563. | n-$C_{12}H_{25}$ | $CH(CH_3)$—$CH_2$—O | H |
| 564. | n-$C_{12}H_{25}$ | $CH(CH_3)$—$CH_2$—O | OH |
| 565. | n-$C_{12}H_{25}$ | $CH_2$—$CH(CH_3)$—O | H |
| 566. | n-$C_{12}H_{25}$ | $CH_2$—$CH(CH_3)$—O | OH |
| 567. | n-$C_{12}H_{25}$ | $CH(C_2H_5)$—$CH_2$—O | H |
| 568. | n-$C_{12}H_{25}$ | $CH(C_2H_5)$—$CH_2$—O | OH |
| 569. | n-$C_{12}H_{25}$ | $C(CH_3)_2$—$CH_2$—O | H |
| 570 | n-$C_{12}H_{25}$ | $C(CH_3)_2$—$CH_2$—O | OH |
| 571. | n-$C_{12}H_{25}$ | $CH_2C(CH_3)_2$—O | H |
| 572. | n-$C_{12}H_{25}$ | $CH_2C(CH_3)_2$—O | OH |
| 573. | n-$C_{12}H_{25}$ | $CH_2$—$CH(C_2H_5)$—O | H |
| 574. | n-$C_{12}H_{25}$ | $CH_2$—$CH(C_2H_5)$—O | OH |
| 575. | n-$C_{13}H_{27}$ | $CH_2$—$CH_2$—O | H |
| 576. | n-$C_{13}H_{27}$ | $CH_2$—$CH_2$—O | OH |
| 577. | n-$C_{13}H_{27}$ | $CH(CH_3)$—$CH_2$—O | H |
| 578. | n-$C_{13}H_{27}$ | $CH(CH_3)$—$CH_2$—O | OH |
| 579. | n-$C_{13}H_{27}$ | $CH_2$—$CH(CH_3)$—O | H |
| 580. | n-$C_{13}H_{27}$ | $CH_2$—$CH(CH_3)$—O | OH |
| 581. | n-$C_{13}H_{27}$ | $CH(C_2H_5)$—$CH_2$—O | H |
| 582. | n-$C_{13}H_{27}$ | $CH(C_2H_5)$—$CH_2$—O | OH |
| 583. | n-$C_{13}H_{27}$ | $C(CH_3)_2$—$CH_2$—O | H |
| 584. | n-$C_{13}H_{27}$ | $C(CH_3)_2$—$CH_2$—O | OH |
| 585. | n-$C_{13}H_{27}$ | $CH_2C(CH_3)_2$—O | H |
| 586. | n-$C_{13}H_{27}$ | $CH_2C(CH_3)_2$—O | OH |
| 587. | n-$C_{13}H_{27}$ | $CH_2$—$CH(C_2H_5)$—O | H |
| 588. | n-$C_{13}H_{27}$ | $CH_2$—$CH(C_2H_5)$—O | OH |
| 589. | n-$C_{14}H_{29}$ | $CH_2$—$CH_2$—O | H |
| 590. | n-$C_{14}H_{29}$ | $CH_2$—$CH_2$—O | OH |
| 591. | n-$C_{14}H_{29}$ | $CH(CH_3)$—$CH_2$—O | H |
| 592. | n-$C_{14}H_{29}$ | $CH(CH_3)$—$CH_2$—O | OH |
| 593. | n-$C_{14}H_{29}$ | $CH_2$—$CH(CH_3)$—O | H |
| 594. | n-$C_{14}H_{29}$ | $CH_2$—$CH(CH_3)$—O | OH |
| 595. | n-$C_{14}H_{29}$ | $CH(C_2H_5)$—$CH_2$—O | H |
| 596. | n-$C_{14}H_{29}$ | $CH(C_2H_5)$—$CH_2$—O | OH |
| 597. | n-$C_{14}H_{29}$ | $C(CH_3)_2$—$CH_2$—O | H |
| 598. | n-$C_{14}H_{29}$ | $C(CH_3)_2$—$CH_2$—O | OH |
| 599. | n-$C_{14}H_{29}$ | $CH_2C(CH_3)_2$—O | H |
| 600. | n-$C_{14}H_{29}$ | $CH_2C(CH_3)_2$—O | OH |
| 601. | n-$C_{14}H_{29}$ | $CH_2$—$CH(C_2H_5)$—O | H |
| 602. | n-$C_{14}H_{29}$ | $CH_2$—$CH(C_2H_5)$—O | OH |
| 603. | n-$C_{15}H_{31}$ | $CH_2$—$CH_2$—O | H |
| 604. | n-$C_{15}H_{31}$ | $CH_2$—$CH_2$—O | OH |
| 605. | n-$C_{15}H_{31}$ | $CH(CH_3)$—$CH_2$—O | H |
| 606. | n-$C_{15}H_{31}$ | $CH(CH_3)$—$CH_2$—O | OH |
| 607. | n-$C_{15}H_{31}$ | $CH_2$—$CH(CH_3)$—O | H |
| 608. | n-$C_{15}H_{31}$ | $CH_2$—$CH(CH_3)$—O | OH |
| 609. | n-$C_{15}H_{31}$ | $CH(C_2H_5)$—$CH_2$—O | H |
| 610. | n-$C_{15}H_{31}$ | $CH(C_2H_5)$—$CH_2$—O | OH |
| 611. | n-$C_{15}H_{31}$ | $C(CH_3)_2$—$CH_2$—O | H |
| 612. | n-$C_{15}H_{31}$ | $C(CH_3)_2$—$CH_2$—O | OH |
| 613. | n-$C_{15}H_{31}$ | $CH_2C(CH_3)_2$—O | H |
| 614. | n-$C_{15}H_{31}$ | $CH_2C(CH_3)_2$—O | OH |
| 615. | n-$C_{15}H_{31}$ | $CH_2$—$CH(C_2H_5)$—O | H |
| 616. | n-$C_{15}H_{31}$ | $CH_2$—$CH(C_2H_5)$—O | OH |
| 617. | n-$C_{16}H_{33}$ | $CH_2$—$CH_2$—O | H |
| 618. | n-$C_{16}H_{33}$ | $CH_2$—$CH_2$—O | OH |
| 619. | n-$C_{16}H_{33}$ | $CH(CH_3)$—$CH_2$—O | H |
| 620. | n-$C_{16}H_{33}$ | $CH(CH_3)$—$CH_2$—O | OH |
| 621. | n-$C_{16}H_{33}$ | $CH_2$—$CH(CH_3)$—O | H |
| 622. | n-$C_{16}H_{33}$ | $CH_2$—$CH(CH_3)$—O | OH |
| 623. | n-$C_{16}H_{33}$ | $CH(C_2H_5)$—$CH_2$—O | H |
| 624. | n-$C_{16}H_{33}$ | $CH(C_2H_5)$—$CH_2$—O | OH |
| 625. | n-$C_{16}H_{33}$ | $C(CH_3)_2$—$CH_2$—O | H |
| 626. | n-$C_{16}H_{33}$ | $C(CH_3)_2$—$CH_2$—O | OH |
| 627. | n-$C_{16}H_{33}$ | $CH_2C(CH_3)_2$—O | H |
| 628. | n-$C_{16}H_{33}$ | $CH_2C(CH_3)_2$—O | OH |
| 629. | n-$C_{16}H_{33}$ | $CH_2$—$CH(C_2H_5)$—O | H |
| 630. | n-$C_{16}H_{33}$ | $CH_2$—$CH(C_2H_5)$—O | OH |
| 631. | iso-$C_3H_7$ | $CH_2$—$CH_2$—O | H |
| 632. | iso-$C_3H_7$ | $CH_2$—$CH_2$—O | OH |
| 633. | iso-$C_3H_7$ | $CH(CH_3)$—$CH_2$—O | H |
| 634. | iso-$C_3H_7$ | $CH(CH_3)$—$CH_2$—O | OH |
| 635. | iso-$C_3H_7$ | $CH_2$—$CH(CH_3)$—O | H |
| 636. | iso-$C_3H_7$ | $CH_2$—$CH(CH_3)$—O | OH |
| 637. | iso-$C_3H_7$ | $CH(C_2H_5)$—$CH_2$—O | H |
| 638. | iso-$C_3H_7$ | $CH(C_2H_5)$—$CH_2$—O | OH |
| 639. | iso-$C_3H_7$ | $C(CH_3)_2$—$CH_2$—O | H |
| 640. | iso-$C_3H_7$ | $C(CH_3)_2$—$CH_2$—O | OH |
| 641. | iso-$C_3H_7$ | $CH_2C(CH_3)_2$—O | H |
| 642. | iso-$C_3H_7$ | $CH_2C(CH_3)_2$—O | OH |
| 643. | iso-$C_3H_7$ | $CH_2$—$CH(C_2H_5)$—O | H |
| 644. | iso-$C_3H_7$ | $CH_2$—$CH(C_2H_5)$—O | OH |
| 645. | iso-$C_4H_9$ | $CH_2$—$CH_2$—O | H |
| 646. | iso-$C_4H_9$ | $CH_2$—$CH_2$—O | OH |
| 647. | iso-$C_4H_9$ | $CH(CH_3)$—$CH_2$—O | H |
| 648. | iso-$C_4H_9$ | $CH(CH_3)$—$CH_2$—O | OH |
| 649. | iso-$C_4H_9$ | $CH_2$—$CH(CH_3)$—O | H |
| 650. | iso-$C_4H_9$ | $CH_2$—$CH(CH_3)$—O | OH |
| 651. | iso-$C_4H_9$ | $CH(C_2H_5)$—$CH_2$—O | H |
| 652. | iso-$C_4H_9$ | $CH(C_2H_5)$—$CH_2$—O | OH |
| 653. | iso-$C_4H_9$ | $C(CH_3)_2$—$CH_2$—O | H |
| 654. | iso-$C_4H_9$ | $C(CH_3)_2$—$CH_2$—O | OH |

TABLE B-continued

| row | $R_1$ | AO | R |
|---|---|---|---|
| 655. | iso-$C_4H_9$ | $CH_2C(CH_3)_2$—O | H |
| 656. | iso-$C_4H_9$ | $CH_2C(CH_3)_2$—O | OH |
| 657. | iso-$C_4H_9$ | $CH_2$—$CH(C_2H_5)$—O | H |
| 658. | iso-$C_4H_9$ | $CH_2$—$CH(C_2H_5)$—O | OH |
| 659. | iso-$C_5H_{11}$ | $CH_2$—$CH_2$—O | H |
| 560 | iso-$C_5H_{11}$ | $CH_2$—$CH_2$—O | OH |
| 661. | iso-$C_5H_{11}$ | $CH(CH_3)$—$CH_2$—O | H |
| 662. | iso-$C_5H_{11}$ | $CH(CH_3)$—$CH_2$—O | OH |
| 663. | iso-$C_5H_{11}$ | $CH_2$—$CH(CH_3)$—O | H |
| 664. | iso-$C_5H_{11}$ | $CH_2$—$CH(CH_3)$—O | OH |
| 665. | iso-$C_5H_{11}$ | $CH(C_2H_5)$—$CH_2$—O | H |
| 666. | iso-$C_5H_{11}$ | $CH(C_2H_5)$—$CH_2$—O | OH |
| 667. | iso-$C_5H_{11}$ | $C(CH_3)_2$—$CH_2$—O | H |
| 668. | iso-$C_5H_{11}$ | $C(CH_3)_2$—$CH_2$—O | OH |
| 669. | iso-$C_5H_{11}$ | $CH_2C(CH_3)_2$—O | H |
| 670. | iso-$C_5H_{11}$ | $CH_2C(CH_3)_2$—O | OH |
| 671. | iso-$C_5H_{11}$ | $CH_2$—$CH(C_2H_5)$—O | H |
| 672. | iso-$C_5H_{11}$ | $CH_2$—$CH(C_2H_5)$—O | OH |
| 673. | iso-$C_6H_{13}$ | $CH_2$—$CH_2$—O | H |
| 674. | iso-$C_6H_{13}$ | $CH_2$—$CH_2$—O | OH |
| 675. | iso-$C_6H_{13}$ | $CH(CH_3)$—$CH_2$—O | H |
| 676 | iso-$C_6H_{13}$ | $CH(CH_3)$—$CH_2$—O | OH |
| 677. | iso-$C_6H_{13}$ | $CH_2$—$CH(CH_3)$—O | H |
| 678. | iso-$C_6H_{13}$ | $CH_2$—$CH(CH_3)$—O | OH |
| 679. | iso-$C_6H_{13}$ | $CH(C_2H_5)$—$CH_2$—O | H |
| 680. | iso-$C_6H_{13}$ | $CH(C_2H_5)$—$CH_2$—O | OH |
| 681. | iso-$C_6H_{13}$ | $C(CH_3)_2$—$CH_2$—O | H |
| 682. | iso-$C_6H_{13}$ | $C(CH_3)_2$—$CH_2$—O | OH |
| 683. | iso-$C_6H_{13}$ | $CH_2C(CH_3)_2$—O | H |
| 684. | iso-$C_6H_{13}$ | $CH_2C(CH_3)_2$—O | OH |
| 685. | iso-$C_6H_{13}$ | $CH_2$—$CH(C_2H_5)$—O | H |
| 686. | iso-$C_6H_{13}$ | $CH_2$—$CH(C_2H_5)$—O | OH |
| 687. | iso-$C_7H_{15}$ | $CH_2$—$CH_2$—O | H |
| 688. | iso-$C_7H_{15}$ | $CH_2$—$CH_2$—O | OH |
| 689. | iso-$C_7H_{15}$ | $CH(CH_3)$—$CH_2$—O | H |
| 690. | iso-$C_7H_{15}$ | $CH(CH_3)$—$CH_2$—O | OH |
| 691. | iso-$C_7H_{15}$ | $CH_2$—$CH(CH_3)$—O | H |
| 692. | iso-$C_7H_{15}$ | $CH_2$—$CH(CH_3)$—O | OH |
| 693. | iso-$C_7H_{15}$ | $CH(C_2H_5)$—$CH_2$—O | H |
| 694. | iso-$C_7H_{15}$ | $CH(C_2H_5)$—$CH_2$—O | OH |
| 695. | iso-$C_7H_{15}$ | $C(CH_3)_2$—$CH_2$—O | H |
| 696. | iso-$C_7H_{15}$ | $C(CH_3)_2$—$CH_2$—O | OH |
| 697. | iso-$C_7H_{15}$ | $CH_2C(CH_3)_2$—O | H |
| 698. | iso-$C_7H_{15}$ | $CH_2C(CH_3)_2$—O | OH |
| 699. | iso-$C_7H_{15}$ | $CH_2$—$CH(C_2H_5)$—O | H |
| 700. | iso-$C_7H_{15}$ | $CH_2$—$CH(C_2H_5)$—O | OH |
| 701. | iso-$C_8H_{17}$ | $CH_2$—$CH_2$—O | H |
| 702. | iso-$C_8H_{17}$ | $CH_2$—$CH_2$—O | OH |
| 703. | iso-$C_8H_{17}$ | $CH(CH_3)$—$CH_2$—O | H |
| 704. | iso-$C_8H_{17}$ | $CH(CH_3)$—$CH_2$—O | OH |
| 705. | iso-$C_8H_{17}$ | $CH_2$—$CH(CH_3)$—O | H |
| 706. | iso-$C_8H_{17}$ | $CH_2$—$CH(CH_3)$—O | OH |
| 707. | iso-$C_8H_{17}$ | $CH(C_2H_5)$—$CH_2$—O | H |
| 708. | iso-$C_8H_{17}$ | $CH(C_2H_5)$—$CH_2$—O | OH |
| 709. | iso-$C_8H_{17}$ | $C(CH_3)_2$—$CH_2$—O | H |
| 710. | iso-$C_8H_{17}$ | $C(CH_3)_2$—$CH_2$—O | OH |
| 711. | iso-$C_8H_{17}$ | $CH_2C(CH_3)_2$—O | H |
| 712. | iso-$C_8H_{17}$ | $CH_2C(CH_3)_2$—O | OH |
| 713. | iso-$C_8H_{17}$ | $CH_2$—$CH(C_2H_5)$—O | H |
| 714. | iso-$C_8H_{17}$ | $CH_2$—$CH(C_2H_5)$—O | OH |
| 715. | iso-$C_9H_{19}$ | $CH_2$—$CH_2$—O | H |
| 716. | iso-$C_9H_{19}$ | $CH_2$—$CH_2$—O | OH |
| 717. | iso-$C_9H_{19}$ | $CH(CH_3)$—$CH_2$—O | H |
| 718. | iso-$C_9H_{19}$ | $CH(CH_3)$—$CH_2$—O | OH |
| 719. | iso-$C_9H_{19}$ | $CH_2$—$CH(CH_3)$—O | H |
| 720. | iso-$C_9H_{19}$ | $CH_2$—$CH(CH_3)$—O | OH |
| 721. | iso-$C_9H_{19}$ | $CH(C_2H_5)$—$CH_2$—O | H |
| 722. | iso-$C_9H_{19}$ | $CH(C_2H_5)$—$CH_2$—O | OH |
| 723. | iso-$C_9H_{19}$ | $C(CH_3)_2$—$CH_2$—O | H |
| 724. | iso-$C_9H_{19}$ | $C(CH_3)_2$—$CH_2$—O | OH |
| 725. | iso-$C_9H_{19}$ | $CH_2C(CH_3)_2$—O | H |
| 726. | iso-$C_9H_{19}$ | $CH_2C(CH_3)_2$—O | OH |
| 727. | iso-$C_9H_{19}$ | $CH_2$—$CH(C_2H_5)$—O | H |
| 728. | iso-$C_9H_{19}$ | $CH_2$—$CH(C_2H_5)$—O | OH |
| 729. | iso-$C_{10}H_{21}$ | $CH_2$—$CH_2$—O | H |
| 730. | iso-$C_{10}H_{21}$ | $CH_2$—$CH_2$—O | OH |
| 731. | iso-$C_{10}H_{21}$ | $CH(CH_3)$—$CH_2$—O | H |
| 732. | iso-$C_{10}H_{21}$ | $CH(CH_3)$—$CH_2$—O | OH |
| 733. | iso-$C_{10}H_{21}$ | $CH_2$—$CH(CH_3)$—O | H |
| 734. | iso-$C_{10}H_{21}$ | $CH_2$—$CH(CH_3)$—O | OH |
| 735. | iso-$C_{10}H_{21}$ | $CH(C_2H_5)$—$CH_2$—O | H |
| 736. | iso-$C_{10}H_{21}$ | $CH(C_2H_5)$—$CH_2$—O | OH |
| 737. | iso-$C_{10}H_{21}$ | $C(CH_3)_2$—$CH_2$—O | H |
| 738. | iso-$C_{10}H_{21}$ | $C(CH_3)_2$—$CH_2$—O | OH |
| 739. | iso-$C_{10}H_{21}$ | $CH_2C(CH_3)_2$—O | H |
| 740. | iso-$C_{10}H_{21}$ | $CH_2C(CH_3)_2$—O | OH |
| 741. | iso-$C_{10}H_{21}$ | $CH_2$—$CH(C_2H_5)$—O | H |
| 742. | iso-$C_{10}H_{21}$ | $CH_2$—$CH(C_2H_5)$—O | OH |
| 743. | iso-$C_{11}H_{23}$ | $CH_2$—$CH_2$—O | H |
| 744. | iso-$C_{11}H_{23}$ | $CH_2$—$CH_2$—O | OH |
| 745. | iso-$C_{11}H_{23}$ | $CH(CH_3)$—$CH_2$—O | H |
| 746. | iso-$C_{11}H_{23}$ | $CH(CH_3)$—$CH_2$—O | OH |
| 747. | iso-$C_{11}H_{23}$ | $CH_2$—$CH(CH_3)$—O | H |
| 748. | iso-$C_{11}H_{23}$ | $CH_2$—$CH(CH_3)$—O | OH |
| 749. | iso-$C_{11}H_{23}$ | $CH(C_2H_5)$—$CH_2$—O | H |
| 750. | iso-$C_{11}H_{23}$ | $CH(C_2H_5)$—$CH_2$—O | OH |
| 751. | iso-$C_{11}H_{23}$ | $C(CH_3)_2$—$CH_2$—O | H |
| 752. | iso-$C_{11}H_{23}$ | $C(CH_3)_2$—$CH_2$—O | OH |
| 753. | iso-$C_{11}H_{23}$ | $CH_2C(CH_3)_2$—O | H |
| 754. | iso-$C_{11}H_{23}$ | $CH_2C(CH_3)_2$—O | OH |
| 755. | iso-$C_{11}H_{23}$ | $CH_2$—$CH(C_2H_5)$—O | H |
| 756. | iso-$C_{11}H_{23}$ | $CH_2$—$CH(C_2H_5)$—O | OH |
| 757. | iso-$C_{12}H_{25}$ | $CH_2$—$CH_2$—O | H |
| 758. | iso-$C_{12}H_{25}$ | $CH_2$—$CH_2$—O | OH |
| 759. | iso-$C_{12}H_{25}$ | $CH(CH_3)$—$CH_2$—O | H |
| 760. | iso-$C_{12}H_{25}$ | $CH(CH_3)$—$CH_2$—O | OH |
| 761. | iso-$C_{12}H_{25}$ | $CH_2$—$CH(CH_3)$—O | H |
| 762. | iso-$C_{12}H_{25}$ | $CH_2$—$CH(CH_3)$—O | OH |
| 763. | iso-$C_{12}H_{25}$ | $CH(C_2H_5)$—$CH_2$—O | H |
| 764. | iso-$C_{12}H_{25}$ | $CH(C_2H_5)$—$CH_2$—O | OH |
| 765. | iso-$C_{12}H_{25}$ | $C(CH_3)_2$—$CH_2$—O | H |
| 766. | iso-$C_{12}H_{25}$ | $C(CH_3)_2$—$CH_2$—O | OH |
| 767. | iso-$C_{12}H_{25}$ | $CH_2C(CH_3)_2$—O | H |
| 768. | iso-$C_{12}H_{25}$ | $CH_2C(CH_3)_2$—O | OH |
| 769. | iso-$C_{12}H_{25}$ | $CH_2$—$CH(C_2H_5)$—O | H |
| 770. | iso-$C_{12}H_{25}$ | $CH_2$—$CH(C_2H_5)$—O | OH |
| 771. | iso-$C_{13}H_{27}$ | $CH_2$—$CH_2$—O | H |
| 772. | iso-$C_{13}H_{27}$ | $CH_2$—$CH_2$—O | OH |
| 773. | iso-$C_{13}H_{27}$ | $CH(CH_3)$—$CH_2$—O | H |
| 774. | iso-$C_{13}H_{27}$ | $CH(CH_3)$—$CH_2$—O | OH |
| 775. | iso-$C_{13}H_{27}$ | $CH_2$—$CH(CH_3)$—O | H |
| 776. | iso-$C_{13}H_{27}$ | $CH_2$—$CH(CH_3)$—O | OH |
| 777. | iso-$C_{13}H_{27}$ | $CH(C_2H_5)$—$CH_2$—O | H |
| 778. | iso-$C_{13}H_{27}$ | $CH(C_2H_5)$—$CH_2$—O | OH |
| 779. | iso-$C_{13}H_{27}$ | $C(CH_3)_2$—$CH_2$—O | H |
| 780. | iso-$C_{13}H_{27}$ | $C(CH_3)_2$—$CH_2$—O | OH |
| 781. | iso-$C_{13}H_{27}$ | $CH_2C(CH_3)_2$—O | H |
| 782. | iso-$C_{13}H_{27}$ | $CH_2C(CH_3)_2$—O | OH |
| 783. | iso-$C_{13}H_{27}$ | $CH_2$—$CH(C_2H_5)$—O | H |
| 784. | iso-$C_{13}H_{27}$ | $CH_2$—$CH(C_2H_5)$—O | OH |
| 785. | iso-$C_{14}H_{29}$ | $CH_2$—$CH_2$—O | H |
| 786. | iso-$C_{14}H_{29}$ | $CH_2$—$CH_2$—O | OH |
| 787. | iso-$C_{14}H_{29}$ | $CH(CH_3)$—$CH_2$—O | H |
| 788. | iso-$C_{14}H_{29}$ | $CH(CH_3)$—$CH_2$—O | OH |
| 789. | iso-$C_{14}H_{29}$ | $CH_2$—$CH(CH_3)$—O | H |
| 790. | iso-$C_{14}H_{29}$ | $CH_2$—$CH(CH_3)$—O | OH |
| 791. | iso-$C_{14}H_{29}$ | $CH(C_2H_5)$—$CH_2$—O | H |
| 792. | iso-$C_{14}H_{29}$ | $CH(C_2H_5)$—$CH_2$—O | OH |
| 793. | iso-$C_{14}H_{29}$ | $C(CH_3)_2$—$CH_2$—O | H |
| 794. | iso-$C_{14}H_{29}$ | $C(CH_3)_2$—$CH_2$—O | OH |
| 795. | iso-$C_{14}H_{29}$ | $CH_2C(CH_3)_2$—O | H |
| 796. | iso-$C_{14}H_{29}$ | $CH_2C(CH_3)_2$—O | OH |
| 797. | iso-$C_{14}H_{29}$ | $CH_2$—$CH(C_2H_5)$—O | H |
| 798. | iso-$C_{14}H_{29}$ | $CH_2$—$CH(C_2H_5)$—O | OH |
| 799. | iso-$C_{15}H_{31}$ | $CH_2$—$CH_2$—O | H |
| 800. | iso-$C_{15}H_{31}$ | $CH_2$—$CH_2$—O | OH |
| 801. | iso-$C_{15}H_{31}$ | $CH(CH_3)$—$CH_2$—O | H |
| 802. | iso-$C_{15}H_{31}$ | $CH(CH_3)$—$CH_2$—O | OH |
| 803. | iso-$C_{15}H_{31}$ | $CH_2$—$CH(CH_3)$—O | H |
| 804. | iso-$C_{15}H_{31}$ | $CH_2$—$CH(CH_3)$—O | OH |
| 805. | iso-$C_{15}H_{31}$ | $CH(C_2H_5)$—$CH_2$—O | H |
| 806. | iso-$C_{15}H_{31}$ | $CH(C_2H_5)$—$CH_2$—O | OH |
| 807. | iso-$C_{15}H_{31}$ | $C(CH_3)_2$—$CH_2$—O | H |
| 808. | iso-$C_{15}H_{31}$ | $C(CH3)_2$—$CH_2$—O | OH |
| 809. | iso-$C_{15}H_{31}$ | $CH_2C(CH_3)_2$—O | H |
| 810. | iso-$C_{15}H_{31}$ | $CH_2C(CH_3)_2$—O | OH |

TABLE B-continued

| row | $R_1$ | AO | R |
|---|---|---|---|
| 811. | iso-$C_{15}H_{31}$ | $CH_2$—$CH(C_2H_5)$—O | H |
| 812. | iso-$C_{15}H_{31}$ | $CH_2$—$CH(C_2H_5)$—O | OH |
| 813. | iso-$C_{16}H_{33}$ | $CH_2$—$CH_2$—O | H |
| 814. | iso-$C_{16}H_{33}$ | $CH_2$—$CH_2$—O | OH |
| 815. | iso-$C_{16}H_{33}$ | $CH(CH_3)$—$CH_2$—O | H |
| 816. | iso-$C_{16}H_{33}$ | $CH(CH_3)$—$CH_2$—O | OH |
| 817. | iso-$C_{16}H_{33}$ | $CH_2$—$CH(CH_3)$—O | H |
| 818. | iso-$C_{16}H_{33}$ | $CH_2$—$CH(CH_3)$—O | OH |
| 819. | iso-$C_{16}H_{33}$ | $CH(C_2H_5)$—$CH_2$—O | H |
| 820. | iso-$C_{16}H_{33}$ | $CH(C_2H_5)$—$CH_2$—O | OH |
| 821. | iso-$C_{16}H_{33}$ | $C(CH_3)_2$—$CH_2$—O | H |
| 822. | iso-$C_{16}H_{33}$ | $C(CH_3)_2$—$CH_2$—O | OH |
| 823. | iso-$C_{16}H_{33}$ | $CH_2C(CH_3)_2$—O | H |
| 824. | iso-$C_{16}H_{33}$ | $CH_2C(CH_3)_2$—O | OH |
| 825. | iso-$C_{16}H_{33}$ | $CH_2$—$CH(C_2H_5)$—O | H |
| 826. | iso-$C_{16}H_{33}$ | $CH_2$—$CH(C_2H_5)$—O | OH |

In a preferred embodiment, the amount of the at least one compound of general formula (I) is in the range of 0.1 to 50% or 0.1 to 49.5% or 0.1 to 49% or 0.1 to 48% or 0.1 to 47% or 0.1 to 46% or 0.1 to 45% or 0.1 to 44% or 0.1 to 43% or 0.1 to 42% or 0.1 to 42% or 0.1 to 41% or 0.1 to 40% or 0.2 to 50% or 0.2 to 49.5% or 0.2 to 49% or 0.2 to 48% or 0.2 to 47% or 0.2 to 46% or 0.2 to 45% or 0.2 to 44% or 0.2 to 43% or 0.2 to 42% or 0.2 to 42% or 0.2 to 41% or 0.2 to 40%, more preferably in the range of 0.1 to 39% or 0.1 to 38% or 0.1 to 37% or 0.1 to 36% or 0.1 to 35% or 0.1 to 34% or 0.1 to 33% or 0.1 to 32% or 0.1 to 31% or 0.1 to 30% or 0.2 to 39% or 0.2 to 38% or 0.2 to 37% or 0.2 to 36% or 0.2 to 35% or 0.2 to 34% or 0.2 to 33% or 0.2 to 32% or 0.2 to 31% or 0.2 to 30% or 0.2 to 29% or 0.5 to 39% or 0.5 to 38% or 0.5 to 37% or 0.5 to 36% or 0.5 to 35% or 0.5 to 34% or 0.5 to 33% or 0.5 to 32% or 0.5 to 31% or 0.5 to 30% or 1 to 39% or 1 to 38% or 1 to 37% or 1 to 36% or 1 to 35% or 1 to 34% or 1 to 33% or 1 to 32% or 1 to 31% or 1 to 30% or 1 to 29% or 1 to 28% or 1 to 27% or 1 to 26% or 1 to 25% or 1 to 24% or 1 to 23% or 1 to 22% or 1 to 21% or 1 to 20% or 1 to 19% or 1 to 18% or 1 to 17% or 1 to 16% or 1 to 15% or 2 to 19% or 2 to 18% or 2 to 17% or 2 to 16% or 2 to 15%, and most preferably in the range of 1 to 14% or 1 to 13% or 1 to 12% or 1 to 11% or 1 to 10% or 2 to 14% or 2 to 13% or 2 to 12% or 2 to 11% or 2 to 10% or 2.5 to 14% or 2.5 to 13% or 2.5 to 12% or 2.5 to 11% or 2.5 to 10%, in each case related to the final weight of the composition.

In another aspect, the presently claimed invention is directed to the use of at least one compound of general formula (I), as described herein above, as adjuvant in the treatment of soil and plants.

'Adjuvant' is understood to be a compound which increases the effectiveness of the biocide, when applied for the treatment of soil and plants. By the term 'effectiveness' it is meant that the adjuvant leads to one or more of the following effects:
  increased biocide activity
  increased biocide absorption and spread on the target surface,
  increased rainfastness of the biocide,
  increased compatibility of the biocide with fertilizer and/or micronutrients and/or other components in the spray solution
  decrease in the phototransformation of the biocide,
  decrease in the amount of driftable droplets from the spray solution
  decrease in the amount of foam in the spray solution By the term 'treatment of soil and plants' it is meant applying the at least one compound of the general formula (I) to soil and plants.

In an embodiment, the presently claimed invention is directed to the use of at least one compound of general formula (Ia), as described herein above, as adjuvant in the treatment of soil and plants.

In another embodiment, the presently claimed invention is directed to the use of at least one compound of general formula (Ib), as described herein above, as adjuvant in the treatment of soil and plants.

In another aspect, the presently claimed invention relates to a method for improving the growth and health of plants characterized in that the plants are treated with the at least one compound of general formula (I), as described herein above.

The term "plant" is to be understood as including wild type plants and plants, which have been modified by either conventional breeding, or mutagenesis or genetic engineering, or by a combination thereof.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

'Improving the growth and health of plants' means that a composition comprising at least one compound of general formula (I) is more effective in controlling the phytopathogenic fungi and/or plant growth and/or undesired insect or mite attack when compared to a composition without at least one compound of general formula (I).

In still another aspect, the presently claimed invention relates to a composition comprising
  (i) at least one biocide and
  (ii) at least one compound of general formula (I), as described herein above.

Biocide

In an embodiment, the at least one biocide is selected from the group of herbicide, insecticide, fungicide, miticide, plant growth regulator and plant growth promoter.

Herbicides are understood as meaning compounds which are active against generally all wild and cultivated plants which are undesired at their particular location (harmful plants). Examples of herbicide are acetochlor, alachlor, butachlor, dimethachlor, dimethenamid, flufenacet, mefenacet, metolachlor, metazachlor, napropamid, naproanilid, pethoxamid, pretilachior, propachlor, thenylchlor; bilanafos, glyphosate, glufosinate, sulfosateamicarbazone, aminotriazole, anilofos, beflubutamid, benazolin, bencarbazone, benfuresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, Drechslera monoceras, endothal, ethofumesate, etobenzanid, fentrazamide, flumiclorac-pentyl, flumioxazin, flupoxam, fluorochloridone, flurtamone, indanofan, isoxaben, propanil, propyzamide, quinclorac, quinmerac, mesotrione, sulcotrione, methylarsonic acid, naptalam, oxadiargyl, oxadiazon, oxaziclomefone, pentoxazone, pinoxaden, pyraclonil, pyraflufen-ethyl, pyrasulfotol, pyrazoxyfen, pyrazolynate, quinoclamine, saflufenacil, sulcotrion, sulfentrazone, terbacil, tefuryltrione, tembotrione, thiencarbazone, topramezon, asulam, butylate, carbetamide, desmedipham, dimepiperate, eptam (EPTC), esprocarb, molinate, orbencarb, phenmedipham, prosulfocarb, pyributicarb, thiobencarb, triallate; bypyridylium, trifluralin, pendimethalin, aclonifen, oxyfluorfen, bromoxynil, butroxydim, clethodim, cethoxydim, tralkoxydim, cycloxydim, profoxydim, clodinaforp-propargyl, cyhalofopbutyl, diclofops, fluazifops, haloxyfops, quizalofops, triclopyr clopyralid, amidosulfuron, azimsulfuron, bensulfuronmethyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron, penoxsulam, metosulam, florasulam, diuron, linuron, atrazine, simazine, terbuthylazine, and salts thereof.

Insecticides are compounds whose effect is targeted particularly against insects and their developmental forms. Examples of insecticide are acephate, azamethiphos, azinphos-methyl, abamectin, bensulide, chlorpyrifos, chlorethoxyfos, chlorpyrifos-methyl, chlorfenvinphos, diazinon, dichlorvos, dicrotophos, dimethoate, disulfoton, ethion, emamectin, fenitrothion, fenthion, isoxathion, malathion, methamidophos, alanycarb, aldicarb, bendiocarb, benfuracarb, carbaryl, carbofuran, carbosulfan, fenamiphos, fenoxycarb, furathiocarb, methiocarb, methomyl, allethrin, bifenthrin, cyfluthrin, cyhalothrin, cyphenothrin, cypermethrin, alpha-cypermethrin, beta-cypermethrin, zeta-cypermethrin, chlorfenapyr, rynaxypyr, avermectin, amitraz, camphechlor, DOT, hexachlorocyclohexane, gamma-hexachlorocyclohexane, methoxychlor, pentachlorophenol, TDE, aldrin, chlordane, chlordecone, dieldrin, endosulfan, endrin, heptacblor, mirex, pyriproxyfen, imidacloprid, clothianidin, thiacloprid, thiamethoxam, fosthiazate, methyl-parathion, mevinphos, naled, omethoate, oxydemeton-methyl, phorate, phosalone, phosmet, phostebupirim, pirimiphos-methyl, profenofos, terbufos, tetrachlorvinphos, tribufos, trichlorfon, spinosad, flonicamid, pymetrozine, transfluthrin, and mixtures thereof.

Fungicides are compounds which kill fungi and their spores or inhibit their growth. Fungicides can either be contact or systemic. A contact fungicide kills fungi when sprayed on its surface. A systemic fungicide has to be absorbed by the fungus before the fungus dies. Examples for suitable fungicides encompass the following species: (3-ethoxypropyl) mercury bromide, 2-methoxyethylmercury chloride, 2-phenylphenol, 8-hydroxyquinoline sulfate, 8-phenylmercuri-oxyquinoline, acibenzolar, acylamino acid fungicides, acypetacs, aldimorph, aliphatic nitrogen fungicides, allyl alcohol, amide fungicides, arnpropylfos, anilazine, anilide fungicides, antibiotic fungicides, aromatic fungicides, aureofungin, azaconazole, azithiram, azoxystrobin, barium polysulfide, benalaxyl, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, basticidin-S, bordeaux mixture, boscalide, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, donatodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, imazapic, imazamox, imazapyr, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, bexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazolefungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Miticides are chemical compounds that kill mites. Antibiotic miticides, carbamate miticides, formamidine miticides, mite growth regulators, organochlorine, permethrin and organophosphate miticides all belong to this category.

Plant growth regulators are chemicals that regulate the plant growth. Plant growth regulators shape the plant, affecting seed growth, time of flowering, the sex of flowers, senescence of leaves and fruits. They also affect which tissues grow upward and which grow downward, leaf formation and stem growth, fruit development and ripening, plant longevity and even plant death. Examples of plant growth regulators are aviglycine, cyanamide, gibberellins such gibberellic acid, quatemary ammonium compounds such as chlormequat chloride, mepiquat chloride and ethylene generators such as ethephone, brassinosteroids, salicylic acid, jasmonates, plant peptide hormones, polyamines, nitric oxide (NO), strigolactones and karrikins.

In an embodiment, the amount of the at least one biocide is in the range of 0.01 to 99.9% by weight of the final weight of the composition.

Solvent

The presence of at least one solvent is optional. The solvent, if present, is selected from the group of water, $C_2$-$C_8$ acyclic or cyclic monoalcohols, $C_3$-$C_8$ acyclic or cyclic ketones, $C_8$- to $C_{30}$-aliphatic hydrocarbons, aromatic or cycloaliphatic $C_7$- to $C_{18}$ compounds, $C_{16}$-$C_{24}$ monocarboxylic acid esters, $C_8$-$C_{26}$ dicarboxylic acid esters, aprotic amines and amides.

Preferably, the solvent is selected from the group of water, ethanol, propanol, isopropanol, butanol, isobutanol, tert-butanol, pentanol, isopentanol, n-hexanol, isohexanol, cyclohexanol, 2-ethylhexanol, acetone, diethyl ketone, tert-butyl methyl ketone, cyclohexanone, n-octane, isooctane, n-decane, isodecane, n-hexadecane, isohexadecane, n-octadecane, iso-octadecane, n-eicosane, isoeicosane, toluene, o-xylene, m-xylene, p-xylene, ethylbenzene, isopropylbenzene, tert-butylbenzene, 2-sec-butylphenol, methyl oleate, ethyl oleate, 2-ethylhexyl laurate, octyl laurate, isopropyl laurate, isopropyl myristate, 2 ethylhexyl palmitate, isopropyl palmitate, butyl stearate, 2-ethylhexyl 2-ethylhexanoate, dimethyl adipate, di-n-butyl adipate, di-n-octyl adipate, bis-(2-ethylhexyl) adipate, di-n-nonyl adipate, di-iso-nonyl adipate, ditridecyl adipate; di-n-octyl succinate, di-iso-octyl succinate, di-(iso-nonyl) cyclohexane-1,2-dicarboxylate, N-methyl-octylpyrrolidone and N-octylpyrrolidone, N,N-dimethyl lactamide and mixtures thereof.

In a preferred embodiment, the amount of the solvent is in the range of 1 to 99% or 1 to 98% or 1 to 97% or 1 to 96% or 1 to 95% or 1 to 94% or 1 to 93% or 1 to 92% or 1 to 91% or 1 to 90% or 5 to 99% or 5 to 98% or 5 to 97% or 5 to 96% or 5 to 95% or 5 to 94% or 5 to 93% or 5 to 92% or 5 to 91% or 5 to 90% or 10 to 99% or 10 to 98% or 10 to 97% or 10 to 96% or 10 to 95% or 10 to 94% or 10 to 93% or 10 to 92% or 10 to 91% or 10 to 90%, more preferably in the range of 20 to 99% or 20 to 98% or 20 to 97% or 20 to 96% or 20 to 95% or 20 to 94% or 20 to 93% or 20 to 92% or 20 to 91% or 20 to 90% or 30 to 99% or 30 to 98% or 30 to 97% or 30 to 96% or 30 to 95% or 30 to 94% or 30 to 93% or 30 to 92% or 30 to 91% or 30 to 90%, even more preferably in the range of 40 to 99% or 40 to 98% or 40 to 97% or 40 to 96% or 40 to 95% or 40 to 94% or 40 to 93% or 40 to 92% or 40 to 91% or 40 to 90%, still more preferably in the range of 50 to 99% or 50 to 98% or 50 to 97% or 50 to 96% or 50 to 95% or 50 to 94% or 50 to 93% or 50 to 92% or 50 to 91% or 50 to 90% or 60 to 99% or 60 to 98% or 60 to 97% or 60 to 96% or 60 to 95% or 60 to 94% or 60 to 93% or 60 to 92% or 60 to 91% or 60 to 90%, and most preferably in the range of 70 to 99% or 70 to 98% or 70 to 97% or 70 to 96% or 70 to 95% or 70 to 94% or 70 to 93% or 70 to 92% or 70 to 91% or 70 to 90% or 70 to 89% or 70 to 88% or 70 to 87% or 70 to 86% or 70 to 85%, in each case related to the final weight of the composition.

Additives/Auxiliaries

The composition of the presently claimed invention may further comprise at least one additive/auxiliary compound selected from the group of solid carriers, thickeners, anti-freezing agents, anti-foaming agents, colorants, sedimentation inhibitors and tackifiers.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide, polysaccharide powders, such as for example cellulose, starch; fertilizers such as ammonium sulfate, ammonium phosphate, ammonium nitrate, urea compounds; products of vegetable origin, such as, but not limited to, cereal meal, tree bark meal, wood meal, nutshell meal, and mixtures thereof.

Suitable thickeners are polysaccharides, for e.g. xanthan gum, carboxymethylcellulose, organic clays (organically modified or unmodified), polycarboxylates and silicates.

Suitable anti-freezing agents are ethylene glycol, propylene glycol, urea and glycerin.

The composition may further comprise anti-foaming agents. Non-limiting examples of suitable anti-foaming agents include silicone emulsions such as for example Silikon SRE from Wacker Germany or Rhodorsil from Rhodia, France; long chain alcohols; fatty acids; salts of fatty acids; organofluorine compounds and their mixtures.

Suitable colorants include both pigments, which are sparingly soluble in water, and dyes, which are soluble in water. Non-limiting examples are Rhodamin B, C. I. Pigment Red 112 and C. I. Solvent Red 1, Pigment Blue 15:4, Pigment Blue 15:3, Pigment Blue 15:2, 35 Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown, 25, Basic Violet 10, Basic Violet 49, Acid Red 51, Acid Red 52, Acid Red 14, Acid Blue 9, Acid Yellow 23, Basic Red 10, Basic Red 108, iron oxide, titanium oxide, iron hexacyanoferrate.

The main purpose of sedimentation inhibitors is rheological stabilization. Sedimentation inhibitors are, for example, but not limited to, bentonite, talcite and herctorites.

Suitable tackifiers or binders are polyvinylpyrrolidons, polyvinylacetates, polyvinyl alcohols, polyacrylates, biological or synthetic waxes, and cellulose ethers.

In another aspect, the presently claimed invention relates to a method of forming a stable composition comprising the step of mixing the at least one compound of general formula (I) with the at least one biocide.

Mixing can be carried out in a manner known per se, for example by homogenizing with suitable devices such as KPG stirrers or magnetic stirrers.

In another aspect, the presently claimed invention relates to a method of forming a stable composition comprising adding the at least one compound of general formula (I) to a tank as a tank mix additive, the tank comprising the biocide.

In an embodiment, individual components of the composition according to the invention may be mixed in a spray tank and further additives/auxiliaries may be added, if appropriate.

In a further embodiment, either individual components of the composition according to the invention or partially premixed components, e.g. components comprising mixtures of the presently claimed invention, may be mixed in a spray tank and further additives/auxiliaries may be added, if appropriate.

In a further embodiment, either individual components of the composition according to the invention or partially premixed components, e. g. components comprising mixtures of the present invention, can be applied jointly (e.g. after tank mix) or consecutively.

In another aspect, the presently claimed invention relates to the use of the composition comprising the at least one biocide and the at least one compound of general formula (I) as adjuvant in the treatment of soil and plants.

In yet another aspect, the presently claimed invention relates to a method for improving the growth and health of plants characterized in that the crops are treated with the composition comprising the at least one biocide and the at least one compound of general formula (I).

The composition according to the presently claimed invention can be applied from a predosage device, a knapsack sprayer, a spray tank, a spray plane, or an irrigation system. Usually, the agrochemical composition is made up with the at least one compound of general formula (I), the at least one biocide, optionally one or more solvents, buffer, and/or further additives/auxiliaries to the desired application concentration and the ready-to-use spray liquor or the agrochemical composition according to the invention is thus obtained. The formulation may be present in the form of an emulsifiable concentrate (EC), a suspo-emulsion (SE), an oil-in-water emulsion (O/W), a water-in-oil emulsion (W/O), an aqueous suspension concentrate (SC), an oil suspension concentrate (OD), a microemulsion (ME) and the like. In an embodiment, 20 to 2000 litres, preferably 50 to 400 litres, of the ready-to-use spray liquid are applied per hectare of agricultural useful area.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection.

Seed treatment techniques include seed dressing, seed coating, seed dusting, seed soaking, and seed pelleting. In furrow applications typically include the steps of making a furrow in cultivated land, seeding the furrow with seeds, applying the composition of the presently claimed invention to the furrow, and closing the furrow. Foliar application refers to the application of the composition of the presently claimed invention to plant foliage, e.g. through spray equipment. For foliar applications, it can be advantageous to modify the behaviour of the pests by use of pheromones in combination with the mixtures of the presently claimed invention.

As used herein, the term "contacting" includes both direct contact (applying the mixtures/compositions directly on the animal pest or plant—typically to the foliage, stem or roots of the plant) and indirect contact (applying the mixtures/compositions to the locus, i.e. habitat, breeding ground, plant, seed, soil, area, material or environment in which a pest is growing or may grow, of the animal pest or plant).

The composition of the presently claimed invention may be applied pre-emergence or post-emergence. Suitably, where the composition is being used to regulate the growth of crop plants, it may be applied pre- or post-emergence, but preferably post-emergence of the crop. Where the composition is used to promote the germination of seeds, it may be applied pre-emergence. The composition can be applied to leaves.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The mixtures of the presently claimed invention can also be used for the treatment of seeds in order to protect the seeds from insect pests, in particular from soil-living insect pests, and the resulting seedling's roots and shoots against soil pests and foliar insects. The presently claimed invention therefore also relates to a method for the protection of seeds from insects, in particular from soil insects, and of the seedling's roots and shoots from insects, in particular from soil and foliar insects, said method comprising treating the seeds before sowing and/or after pregermination with the composition of the presently claimed invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active mixture is carried out by spraying or by dusting the seeds before sowing of the plants and before emergence of the plants.

The critical micelle concentrations (CMC) is determined by monitoring the decrease of the air-liquid interfacial tension vs. surfactant concentration, where the surface tension is measured according to ISO 304-1985 (2) by the plate method.

Surface tension measurements were done with a solution or dispersion of 1 g/l of the compound in deionized water. The static or equilibrium surface tension is a characteristic value of the interfacial activity of a formulation in the spray solution. Below the critical micelle concentration (CMC) the static surface tension depends on the concentration of the surface-active ingredients in the formulation, whereas above the CMC the static surface tension stays constant. The measurement was carried out with the process tensiometer Kruess K 100 using the Wilhelmy-Plate-Method. During the measurement the bottom line of a vertical hanging platinum plate is wetted by the liquid to be analysed. The force with which the plate is pulled into the liquid is measured and can be converted into the surface tension of the liquid in mN/m. 40 mL of the prepared spray solution are filled into Teflon troughs in the apparatus and the surface tension is detected. The static surface tension is calculated once five successive measuring points match within 0.1 mN/m.

Advantages

1. Improved human and environmental toxicity versus NPEs.
2. The compounds of general formula (I) have a wide application and can be used with a range of biocides.

EMBODIMENTS

1. A compound of general formula (I)

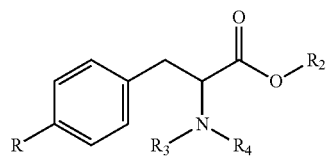

(I)

wherein in

R denotes H, OH or $OR_5$, wherein $R_5$ is $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39; and $R_2$ denotes linear or branched, substituted or unsubstituted $C_1$-$C_{16}$ alkyl or linear or branched, substituted or unsubstituted $C_2$-$C_{16}$ alkenyl;

$R_3$ denotes H or $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

$R_4$ denotes $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

or $R_2$ denotes $(AO)_n$—H wherein (AO) is independently $CH_2$—$CH_2$—O, $CH(CH_3)$—$CH_2$—O, $CH_2$—$CH(CH_3)$—O, $CH(C_2H_5)$—$CH_2$—O, $C(CH_3)_2$—$CH_2$—O, $CH_2C(CH_3)_2$—O or $CH_2$—$CH(C_2H_5)$—O, and n is an integer in the range from 1 to 39;

$R_3$ denotes H;

$R_4$ denotes —$C(=O)R_1$, wherein $R_5$ is linear or branched, unsubstituted $C_2$-$C_{16}$ alkyl.

2. The compound according to embodiment 1, wherein R is H or OH.
3. The compound according to embodiment 1, wherein $R_2$ is selected from the group of methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, isotetradecyl; isopentadecyl and isohexadecyl, $R_3$ is H and $R_4$ is $(AO)_n$—H, wherein (AO) is selected from the group of $CH_2$—$CH_2$—O, $CH(CH_3)$—$CH_2$—O, $CH_2$—$CH(CH_3)$—O, and n is an integer in the range from 1 to 39.
4. The compound according to embodiment 1, wherein $R_2$ is $(AO)_n$—H, wherein (AO) is independently $CH_2$—$CH_2$—O, $CH(CH_3)$—$CH_2$—O, or $CH_2$—$CH(CH_3)$—O, and n is an integer in the range from 1 to 39; $R_3$ is H and $R_4$ is $C(=O)R_1$, wherein $R_1$ is selected from the group of ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, iso-tetradecyl; isopentadecyl and isohexadecyl.
5. The compound according to one or more of embodiment 1 to 4, wherein (AO) is $CH_2$—$CH_2$—O.
6. The compound according to one or more of embodiment 1 to 4, wherein n is an integer in the range from 2 to 30.
7. Use of the at least one compound of general formula (I) according to one or more of embodiments 1 to 6, as adjuvant in the treatment of soil and plants.
8. A method for improving the growth and health of plants characterized in that the crops are treated with the at least one compound of general formula (I) according to one or more of embodiments 1 to 6.
9. A composition comprising
    (i) at least one biocide and
    (ii) at least one compound of general formula (I) according to one or more of embodiments 1 to 6.
10. The composition according to embodiment 9, wherein the at least one biocide is selected from the group of herbicide, insecticide, fungicide, miticide, plant growth regulator and plant growth promoter.
11. The composition according to one or more of embodiments 9 to 10, wherein the amount of the at least one biocide is in the range of 0.01 to 99.9% by weight of the final weight of the composition.
12. The composition according to embodiment 9, wherein the amount of the at least one compound of general formula (I) is in the range of 0.1 to 50% by weight of the final weight of the composition.
13. The composition according to one or more of embodiments 9 to 12, further comprising at least one solvent.
14. The composition according to embodiment 13, wherein the at least one solvent is selected from the group of water, $C_2$-$C_8$ acyclic or cyclic monoalcohols, $C_3$-$C_8$ acyclic or cyclic ketones, $C_8$- to $C_{30}$-aliphatic hydrocarbons, aromatic or cycloaliphatic $C_7$ to $C_{18}$ compounds, $C_{16}$-$C_{24}$ monocarboxylic acid esters, $C_8$-$C_{26}$ dicarboxylic acid esters, aprotic amines and amides.
15. The composition according to one or more of embodiments 13 or 14, wherein the at least one solvent is selected from the group of water, ethanol, propanol, isopropanol, butanol, isobutanol, tert butanol, pentanol, isopentanol, n-hexanol, isohexanol, cyclohexanol, 2-ethylhexanol, acetone, diethyl ketone, tert-butyl methyl ketone, cyclohexanone, n-octane, isooctane, n-decane, isodecane, n-hexadecane, isohexadecane, n-octadecane, iso-octadecane, n-eicosane, isoeicosane, toluene, o-xylene, m-xylene, p-xylene, ethylbenzene, isopropylbenzene, tert-butylbenzene, 2-sec-butylphenol, methyl oleate, ethyl oleate, 2-ethylhexyl laurate, octyl laurate, isopropyl laurate, isopropyl myristate, 2 ethylhexyl palmitate, isopropyl palmitate, butyl stearate, 2-ethylhexyl 2-ethylhexanoate, dimethyl adipate, di-n-butyl adipate, di-n-octyl adipate, bis-(2-ethylhexyl) adipate, di-n-nonyl adipate, di-iso-nonyl adipate, ditridecyl adipate; di-n-octyl succinate, di-iso-octyl succinate, di-(iso-nonyl) cyclohexane-1,2-dicarboxylate, N-methyl-octylpyrrolidone and N-octylpyrrolidone and N, N-dimethyl lactamide.

16. A method of forming a stable composition according to one or more of embodiments 9 to 15, the method comprising the step of mixing the at least one compound of general formula (I) with the at least one biocide.

17. A method of forming a stable composition according to one or more of embodiments 9 to 15, the method comprising adding the at least one compound of general formula (I) to a tank as a tank mix additive, the tank comprising the biocide.

18. Use of the composition according to one or more of embodiments 9 to 15, as adjuvant in the treatment of soil and plants.

19. A method for improving the growth and health of plants characterized in that the crops are treated with the composition according to one or more of embodiments 9 to 15.

Examples

Compounds
Phenylalanine and tyrosine were purchased from Sigma Aldrich.
Touchdown HiTech®
Flexstar®
were obtained from Syngenta
Methods
Critical Micelle Concentration (CMC)

The critical micelle concentration (CMC) is determined by monitoring the decrease of the air-liquid interfacial tension vs. surfactant concentration, where the surface tension is measured according to ISO 304-1985 (2) by the plate method.

Surface Tension

Physical measurements were done with a solution or dispersion of 1 g/l of the compound in deionized water. The static or equilibrium surface tension is a characteristic value of the interfacial activity of a formulation in the spray solution. Below the critical micelle concentration (CMC) the static surface tension depends on the concentration of the surface-active ingredients in the formulation, whereas above the CMC the static surface tension stays constant. The measurement was carried out with the process tensiometer Kruess K 100 using the Wilhelmy-Plate-Method. During the measurement the bottom line of a vertical hanging platinum plate is wetted by the liquid to be analysed. The force with which the plate is pulled into the liquid is measured and can be converted into the surface tension of the liquid in mN/m. 40 mL of the prepared spray solution are filled into Teflon troughs in the apparatus and the surface tension is detected. The static surface tension is calculated once five successive measuring points match within 0.1 mN/m.

General Procedure for Synthesis of Compounds of General Formula (I)

Synthesis of Ester

To a four-neck round bottom flask equipped with a condenser, dean-stark trap, nitrogen inlet, thermocouple and overhead stirrer was charged amino acid (1 mol) and fatty alcohol (2.5 mol). The reaction was heated to 120° C. Methanesulfonic acid (1.3 mol) was added to the reaction mixture at 120° C. followed by stirring at this temperature for two hours. The reaction mixture was poured into an excess of hexane, followed by stirring at room temperature and then filtered. The precipitate was washed with diethyl ether and dried.

Synthesis of Amide by a. Carboxylic Acid Route

To a four-neck round bottom flask equipped with a condenser, dean-stark trap, nitrogen inlet, thermocouple, and overhead stirrer was charged amino acid (1 mol), NaOH (1.1 mol) and fatty acid (2 mol). Xylene (3-4 volumes) was added as a solvent. The reaction mixture was heated to 150° C. for 16 hours. It was acidified to a neutral pH and the resulting product was concentrated under vacuum until residual fatty acid and xylene were removed.

b. Carboxylic Acid Chloride Route

To a four-neck round bottom flask equipped with a condenser, nitrogen inlet, thermocouple and overhead stirrer was charged amino acid (1 mol) and an aqueous solution of sodium hydroxide (15%). The solution was cooled to 0° C., and a stoichiometric amount of acid chloride (0.5 mol to 1 mol) was added over such a period of time that the temperature of reaction remained below 10° C. The solution was allowed to return to room temperature and stirred for an additional hour. The resulting reaction was acidified with concentrated hydrochloric acid and the precipitate was filtered. The precipitate was then washed with 0.1N HCl (3×), deionized water (3×) and diethyl ether (3×).

Synthesis of Alkoxylated Compounds of General Formula (I)

A high pressure stainless steel autoclave of 2-gallon capacity, 2757 kpa (400-psi) maximum pressure and 450° C. *maximum* temperatures was utilized to achieve the ethoxylation reaction.

1 mole of ester amide was charged into a high pressure stainless steel autoclave along with a solution of 0.02 moles of sodium methoxide 25%, in methanol. Temperature was then increased to 120° C. with continuous stirring. A stream of nitrogen gas was passed through the system for two minutes to flush out air and raise pressure to 34-psi. The nitrogen stream was then replaced by ethylene oxide at a rate, which was regulated by monitoring the pressure in the autoclave. The reaction was carried out for different intervals of time, allowing the temperature to raise to 150-180° C. After a constant pressure was realized, vacuum was applied to remove any residual ethylene oxide for half an hour. Vacuum was broken with a stream of nitrogen, and the reaction was cooled. After cooling, the obtained product was discharged, and weighed. The total number of ethylene oxide (EO) was 5, 10, 20 and 22, for phenylalanine and tyrosine as confirmed by $H^1$ NMR and GC-MS.

TABLE-I

| Compound | Amino acid | No. of moles of EO | Fatty acid chain length | Linkage type: ester or amide | Physical state | CMC (mmol/L) | Surface tension @ 1000 ppm |
|---|---|---|---|---|---|---|---|
| Example 1 | Phenylalanine | 5 | $C_6$ | amide | liquid | 51.5 | 41.5 |
| Example 2 | Phenylalanine | 10 | $C_6$ | amide | liquid | NA | 37.4 |
| Example 3 | Phenylalanine | 22 | $C_6$ | amide | liquid | NA | 38.5 |
| Example 4 | Phenylalanine | 10 | $C_{8/10}$ | amide | solid | 46.3 | 30.2 |
| Example 5 | Phenylalanine | 20 | $C_{8/10}$ | amide | solid | 82.2 | 31.1 |
| Example 6 | Phenylalanine | 5 | $C_{8/10}$ | amide | liquid | 716.9 | 29.9 |
| Example 7 | Phenylalanine | 10 | $C_{8/10}$ | amide | liquid | 47.7 | 31.6 |
| Example 8 | Phenylalanine | 20 | $C_{8/10}$ | amide | liquid | 177.5 | 32.4 |
| Example 9 | Phenylalanine | 5 | $C_{12}$ | amide | liquid | 83.5 | 28.3 |
| Example 10 | Phenylalanine | 20 | $C_{12}$ | amide | liquid | 32.0 | 68.3 |

Evaluation of herbicidal efficacy in field trial

Touchdown HiTech® (Glyphosate herbicide): Rate 0.56 LB AE/A

Flexstar® (Glyphosate, Fomesafen herbicide): 0.147 LB AI/A

Compound of Example 8: 0.5% v/v

Compound of Example 10: 0.5% v/v

Commercially available non-ionic adjuvant based on alcohol alkoxylates: 0.5% v/v

TABLE-II

| Composition Plant | No. of days | Example 11 Touchdown HiTech® + Flexstar® % Control, Mean | Example 12 Touchdown HiTech® + Flexstar® + compound of example 8 % Control, Mean | Example 13 Touchdown HiTech® + Flexstar® + compound of example 10 % Control, Mean | Example 14 Commercially available non-ionic adjuvant based on alcohol alkoxylates % Control, Mean |
|---|---|---|---|---|---|
| Soybean | 7 DA A | 11.3 | 15.8 | 15.0 | 19.0 |
|  | 14 DA A | 5.0 | 7.0 | 6.8 | 10.3 |
|  | 22 DA A | 0.0 | 0.0 | 0.0 | 0.0 |
| Amaranth, Palmer | 7 DA A | 70.0 | 81.3 | 83.8 | 83.0 |
|  | 14 DA A | 65.0 | 76.3 | 78.0 | 81.3 |
|  | 22 DA A | 47.5 | 55.0 | 51.3 | 58.8 |
| Crabgrass, large | 7 DA A | 82.5 | 86.3 | 88.8 | 84.3 |
|  | 14 DA A | 93.5 | 98.0 | 97.3 | 97.0 |
|  | 22 DA A | 96.5 | 98.5 | 99.0 | 98.5 |
| Lambsquarter, common | 7 DA A | 75.0 | 87.3 | 86.3 | 90.0 |
|  | 14 DA A | 87.5 | 95.8 | 98.0 | 96.5 |
|  | 22 DA A | 99.0 | 99.0 | 99.0 | 99.0 |

Dicamba/Glyphosate tolerant soybeans, variety Asgrow 30X6, were used. An increase in the % control value for examples 12 and 13 indicates that all the four plant varieties were controlled better with the treatments containing adjuvants of example 8 and 10 compared to the control example 11. For soybean plant, a value of zero after 22 days indicates that the soybeans fully recovered and there was no damage to the soybean plants.

The compounds of the present invention exhibited adjuvancy for glyphosate/fomesafen against Palmer amaranth, large crabgrass and common lambsquarter.

Further, the compounds of the present invention exhibited an adjuvancy equivalent to the commercially available non-ionic adjuvant based on alcohol alkoxylates (example 14) as there was no statistically significant difference in the percentage control values of plant treatments with compounds of the present invention and that of the commercial adjuvant.

The invention claimed is:

1. A compound of general formula (I)

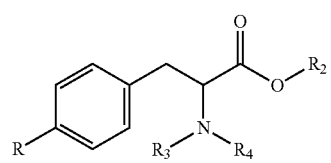

(I)

wherein

R denotes H, OH or $OR_5$, wherein $R_5$ is $(AO)_n$—H, wherein each (AO) is independently $CH_2$—$CH_2$—O, $CH(CH_3)$—$CH_2$—O, $CH_2$—$CH(CH_3)$—O, $CH(C_2H_5)$ CH$_2$—O, C(CH$_3$)$_2$—CH$_2$—O, CH$_2$C(CH$_3$)$_2$—O, or CH$_2$—CH(C$_2$H$_5$)—O, and n is an integer in the range from 5 to 36;
and R$_2$ selected from the group of methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, isotetradecyl; isopentadecyl, isohexadecyl;

R$_3$ denotes H or (AO)$_n$—H, wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O, or CH$_2$—CH(C$_2$H$_5$)—O, and n is an integer in the range from 5 to 36; and R$_4$ denotes (AO)$_n$—H, wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 5 to 36;
or R$_2$ denotes (AO)$_n$—H, wherein (AO) is independently CH$_2$—CH$_2$—O, CH(CH$_3$)—CH$_2$—O, CH$_2$—CH(CH$_3$)—O, CH(C$_2$H$_5$)—CH$_2$—O, C(CH$_3$)$_2$—CH$_2$—O, CH$_2$C(CH$_3$)$_2$—O or CH$_2$—CH(C$_2$H$_5$)—O, and n is an integer in the range from 5 to 36;

R$_3$ denotes H; and

R$_4$ denotes —C(=O)R$_1$, wherein R$_1$ is linear or branched, unsubstituted C$_2$-C$_{16}$ alkyl.

2. The compound according to claim 1, wherein R is H or OH.

3. The compound according to claim 1, wherein R$_2$ is selected from the group consisting of methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, isobutyl, isopentyl, isohexyl, isoheptyl, isooctyl, isononyl, isodecyl, isoundecyl, isododecyl, isotridecyl, isotetradecyl, isopentadecyl, isohexadecyl, and mixtures thereof, and
wherein R$_3$ is H, and R$_4$ is (AO)$_n$—H, wherein (AO) is selected from the group consisting of CH$_2$—CH$_2$—O, CH(CH$_3$)—CH$_2$—O, CH$_2$—CH(CH$_3$)—O, and mixtures thereof, and n is an integer in the range from 5 to 36.

4. The compound according to claim 1, wherein (AO) is CH$_2$—CH$_2$—O.

5. A method of using the at least one compound of general formula (I) according to claim 1, the method comprising using the at least one compound of general formula (I) for the treatment of soil and plants.

6. A method for improving the growth and health of plants, wherein the method comprises treating the plants with the at least one compound of general formula (I) according to claim 1.

7. A composition comprising
(i) at least one biocide; and
(ii) at least one compound of general formula (I) according to claim 1.

8. The composition according to claim 7, wherein the at least one biocide is selected from the group consisting of herbicide, insecticide, fungicide, miticide, plant growth regulator, and plant growth promoter.

9. The composition according to claim 7, wherein the amount of the at least one biocide is in the range of 0.01 to 99.9% by weight of the final weight of the composition.

10. The composition according to claim 7, wherein the amount of the at least one compound of general formula (I) is in the range of 0.1 to 50% by weight of the final weight of the composition.

11. The composition according to claim 7, further comprising at least one solvent.

12. The composition according to claim 11, wherein the at least one solvent is selected from the group consisting of water, C$_2$-C$_8$ acyclic or cyclic monoalcohols, C$_3$-C$_8$ acyclic or cyclic ketones, C$_8$-C$_{30}$-aliphatic hydrocarbons, aromatic or cycloaliphatic C$_7$-C$_{18}$ compounds, C$_{16}$-C$_{24}$ monocarboxylic acid esters, C$_8$-C$_{26}$ dicarboxylic acid esters, aprotic amines, amides, and mixtures thereof.

13. The composition according to claim 11, wherein the at least one solvent is selected from the group consisting of water, ethanol, propanol, isopropanol, butanol, isobutanol, tert butanol, pentanol, isopentanol, n-hexanol, isohexanol, cyclohexanol, 2-ethylhexanol, acetone, diethyl ketone, tert-butyl methyl ketone, cyclohexanone, n-octane, isooctane, n-decane, isodecane, n-hexadecane, isohexadecane, n-octadecane, iso-octadecane, n-eicosane, isoeicosane, toluene, o-xylene, m-xylene, p-xylene, ethylbenzene, isopropylbenzene, tert-butylbenzene, 2-sec-butylphenol, methyl oleate, ethyl oleate, 2-ethylhexyl laurate, octyl laurate, isopropyl laurate, isopropyl myristate, 2 ethylhexyl palmitate, isopropyl palmitate, butyl stearate, 2-ethylhexyl 2-ethylhexanoate, dimethyl adipate, di-n-butyl adipate, di-n-octyl adipate, bis-(2-ethylhexyl) adipate, di-n-nonyl adipate, di-iso-nonyl adipate, ditridecyl adipate; di-n-octyl succinate, di-iso-octyl succinate, di-(iso-nonyl) cyclohexane-1,2-dicarboxylate, N-methyl-octylpyrrolidone and N-octylpyrrolidone, N, N-dimethyl lactamide, and mixtures thereof.

14. A method of forming a stable composition according to claim 7, the method comprising the step of mixing the at least one compound of general formula (I) with the at least one biocide.

15. A method of forming a stable composition according to claim 7, the method comprising adding the at least one compound of general formula (I) to a tank as a tank mix additive, wherein the tank contains the biocide.

16. A method of using the composition according to claim 7, the method comprising using the composition as an adjuvant in the treatment of soil and plants.

17. A method for improving the growth and health of plants, the method comprising treating the plants with the composition of claim 7.

18. The compound according to claim 1, wherein the compound is useful as an adjuvant in a treatment of soil and plants.

* * * * *